(12) United States Patent
Stancer et al.

(10) Patent No.: US 8,494,649 B2
(45) Date of Patent: Jul. 23, 2013

(54) CONTROLLING EFFECTS CAUSED BY EXPOSURE OF AN IMPLANTABLE MEDICAL DEVICE TO A DISRUPTIVE ENERGY FIELD

(75) Inventors: Christopher C. Stancer, Prescott, WI (US); Piotr J. Przybyszewski, Coon Rapids, MN (US); Sandy K. Wixon, Andover, MN (US); Joel Peltier, Lindstrom, MN (US); Sung-Min Park, Blaine, MN (US); David E. Manahan, St. Paul, MN (US); Jonathan Edmonson, Blaine, MN (US); Ben W. Herberg, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 410 days.

(21) Appl. No.: 12/828,081

(22) Filed: Jun. 30, 2010

(65) Prior Publication Data

US 2011/0106217 A1 May 5, 2011

Related U.S. Application Data

(60) Provisional application No. 61/256,804, filed on Oct. 30, 2009, provisional application No. 61/256,794, filed on Oct. 30, 2009.

(51) Int. Cl.
*A61N 1/05* (2006.01)
(52) U.S. Cl.
USPC ............ 607/63; 600/411; 607/116; 607/122; 128/901; 128/908
(58) Field of Classification Search
None
See application file for complete search history.

(56) References Cited

U.S. PATENT DOCUMENTS

| 4,374,382 | A | | 2/1983 | Markowitz |
| 5,117,824 | A | | 6/1992 | Keimel et al. |
| 5,333,095 | A | * | 7/1994 | Stevenson et al. ............ 361/302 |
| 5,545,186 | A | | 8/1996 | Olson et al. |
| 5,755,736 | A | | 5/1998 | Gillberg et al. |
| 5,787,452 | A | | 7/1998 | McKenna |
| 7,187,535 | B1 | | 3/2007 | Iyer et al. |
| 7,214,068 | B2 | | 5/2007 | Kronich et al. |
| 7,294,785 | B2 | | 11/2007 | Uutela et al. |
| 7,363,090 | B2 | * | 4/2008 | Halperin et al. ............. 607/116 |
| 7,539,004 | B2 | | 5/2009 | Iyer et al. |
| 2005/0154421 | A1 | | 7/2005 | Ousdigian |

(Continued)

OTHER PUBLICATIONS

Office Action from U.S. Appl. No. 12/828,097 dated Aug. 31, 2012 (11 pages).

(Continued)

*Primary Examiner* — Kennedy Schaetzle
(74) *Attorney, Agent, or Firm* — Stephen W. Bauer; Michael J. Ostrom

(57) ABSTRACT

Techniques are described for controlling effects caused when an implantable medical device (IMD) is subject to a disruptive energy field. The IMD may include an implantable lead that includes one or more electrodes. The IMD may further include a first component having a parasitic inductance. The IMD may further include a second component having a reactance. In some examples, the reactance of the second component may be selected based on the parasitic inductance of the first component such that an amount of energy reflected along the lead in response to energy produced by an electromagnetic energy source is below a selected threshold. In additional examples, the parasitic inductance of the first component and the reactance of the second component are configured such that an amount of energy reflected along the lead in response to a frequency of electromagnetic energy is below a selected threshold.

38 Claims, 13 Drawing Sheets

U.S. PATENT DOCUMENTS

| | | | |
|---|---|---|---|
| 2005/0283213 | A1 | 12/2005 | Gray |
| 2006/0009819 | A1 | 1/2006 | Przybyszewski |
| 2006/0247684 | A1* | 11/2006 | Halperin et al. .................. 607/2 |
| 2007/0021814 | A1 | 1/2007 | Inman et al. |
| 2007/0083244 | A1 | 4/2007 | Stevenson et al. |
| 2007/0112398 | A1* | 5/2007 | Stevenson et al. ............. 607/63 |
| 2007/0203530 | A1* | 8/2007 | Hubing et al. ................. 607/37 |
| 2008/0058902 | A1 | 3/2008 | Gray |
| 2008/0132986 | A1 | 6/2008 | Gray et al. |
| 2008/0269591 | A1* | 10/2008 | Halperin et al. ............. 600/407 |
| 2009/0128987 | A1 | 5/2009 | Zhao et al. |
| 2010/0138192 | A1* | 6/2010 | Min ................................ 703/1 |
| 2011/0106218 | A1* | 5/2011 | Stancer et al. ................. 607/63 |
| 2012/0059445 | A1* | 3/2012 | Stevenson et al. ............ 607/116 |

OTHER PUBLICATIONS

International Preliminary Report on Patentability from corresponding PCT Application Serial No. PCT/US2010/054242 dated Feb. 15, 2012 (21 pages).

Reply to Written Opinion dated Mar. 2, 2011, from international application No. PCT/US2010/054242, filed Aug. 30, 2011, 14 pp.

U.S. Appl. No. 12/828,097, by Christopher C. Stancer, filed Jun. 30, 2010.

Declaration Under 37 C.F.R. 1.132 for U.S. Appl. No. 12/828,081, by Sung-Min Park, dated Mar. 28, 2013 (5 pages).

Response filed on May 8, 2013 in response to Office Action dated Feb. 8, 2013 from U.S. Appl. No. 12/828,097 (14 pages).

Amendment in response to Office Action dated Aug. 31, 2012 for U.S. Appl. No. 12/828,097 filed Nov. 30, 2012 (19 pages).

Final Office Action from U.S. Appl. No. 12/828,097, dated Feb. 8, 2013, 7 pp.

International Search Report and Written Opinion from corresponding Application Serial No. PCT/US2010/054242, dated Mar. 2, 2011 (11 pages).

* cited by examiner

CONTROLLING EFFECTS CAUSED BY EXPOSURE OF AN IMPLANTABLE MEDICAL DEVICE TO A DISRUPTIVE ENERGY FIELD

RELATED APPLICATIONS

This application claims the benefit of U.S. Provisional Application No. 61/256,804, filed Oct. 30, 2009, and of U.S. Provisional Application No. 61/256,794, filed Oct. 30, 2009, the contents of which are hereby incorporated by reference in their entirety.

TECHNICAL FIELD

The disclosure relates to implantable medical devices, and more particularly, to controlling effects caused by exposure of an implantable medical device to a disruptive energy field.

BACKGROUND

Some types of implantable medical devices (IMDs) provide therapeutic electrical stimulation to and/or monitor activity of a tissue of a patient via electrodes of one or more implantable leads that include electrodes. Examples of such devices include implantable cardiac pacemakers, cardioverters, defibrillators, neurostimulators, muscle stimulators, or the like. In the case of therapeutic electrical stimulation, the electrical stimulation may be delivered to the tissue via the electrodes of implantable leads in the form of neurostimulation pulses, pacing pulses, cardioversion shocks, defibrillation shocks, cardiac resynchronization or other signals. In some cases, electrodes carried by the implantable leads may be used to sense one or more physiological signals to monitor the condition of a patient and/or to control delivery of therapeutic electrical stimulation based on the sensed signals.

An IMD may be exposed to a disruptive energy field for any of a number of reasons. For example, one or more medical procedures may need to be performed on the patient within whom the IMD is implanted for purposes of diagnostics or therapy. For example, the patient may need to have a magnetic resonance imaging (MRI) scan, computed tomography (CT) scan, electrocautery, diathermy or other medical procedure that produces a magnetic field, electromagnetic field, electric field or other disruptive energy field.

The disruptive energy field may induce energy on one or more of the implantable leads coupled to the IMD, which could alter the operation of the IMD. For example, the induced energy may produce lead heating, radio frequency (RF) rectification, and/or device heating effects, which could alter the pacing and/or sensing thresholds within the IMD.

SUMMARY

In general, this disclosure is directed to techniques for configuring one or more components within an implantable medical device (IMD) such that effects are controlled and/or reduced when the device is subject to a disruptive energy field. In some examples, the disruptive energy field may be a magnetic or radio frequency (RF) field generated by an electromagnetic energy source. In additional examples, the disruptive energy field may be an energy field produced by a medical imaging modality, such as, e.g., a magnetic resonance imaging (MRI) modality. The energy from the electromagnetic energy source may induce current flow within electrical components of the lead, which can produce lead heating, RF rectification, device heating and other effects.

Certain components within the IMD, although not primarily considered as inductive and/or capacitive components for conventional implantable device design, may nevertheless produce parasitic inductances and/or capacitances. The parasitic inductances and/or capacitances of such components may be utilized to deliberately design an electrical network that reduces the amount of electromagnetic energy reflected along a lead by the IMD for a given frequency or range of frequencies, and thereby reduce the effects caused by the disruptive energy field such as, e.g., lead heating, device rectification, or device heating.

When an IMD is placed within the presence of a disruptive energy field, the electromagnetic waves and/or energy associated with the field may propagate along the length of a lead towards the housing of the IMD. The electrical components within the device housing may reflect a substantial portion of the electromagnetic wave along the lead toward the electrodes. Because the techniques described in this disclosure may help to reduce the amount of reflected energy in the implanted lead, the techniques of this disclosure may be used to control the effects caused by placing the device in the presence of disruptive energy field.

In one aspect, the disclosure is directed to a method that includes determining a parasitic inductance for a first component within an IMD that includes a lead that includes one or more electrodes. The method further includes selecting a reactance for a second component within the IMD based on the parasitic inductance such that an amount of energy reflected along the lead in response to energy emitted by an electromagnetic energy source is below a selected threshold.

In another aspect, the disclosure is directed to an IMD that includes an implantable lead that includes one or more electrodes. The device further includes a first component having a parasitic inductance. The device further includes a second component having a reactance selected based on the parasitic inductance such that an amount of energy reflected along the lead in response to energy emitted by an electromagnetic energy source is below a selected threshold.

In another aspect, the disclosure is directed to a method that includes selecting a frequency of energy emitted by an electromagnetic energy source. The method further includes configuring a parasitic inductance of a first component and a reactance of a second component within the IMD such that an amount of energy reflected along the lead in response to the selected frequency of the energy is below the selected threshold.

In another aspect, the disclosure is directed to an IMD that includes an implantable lead that includes one or more electrodes. The device further includes a first component having a parasitic inductance. The device further includes a second component having a reactance, wherein the parasitic inductance of the first component and the reactance of the second component are configured such that an amount of energy reflected along the lead in response to a frequency of energy produced by an electromagnetic energy source is below the a selected threshold.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
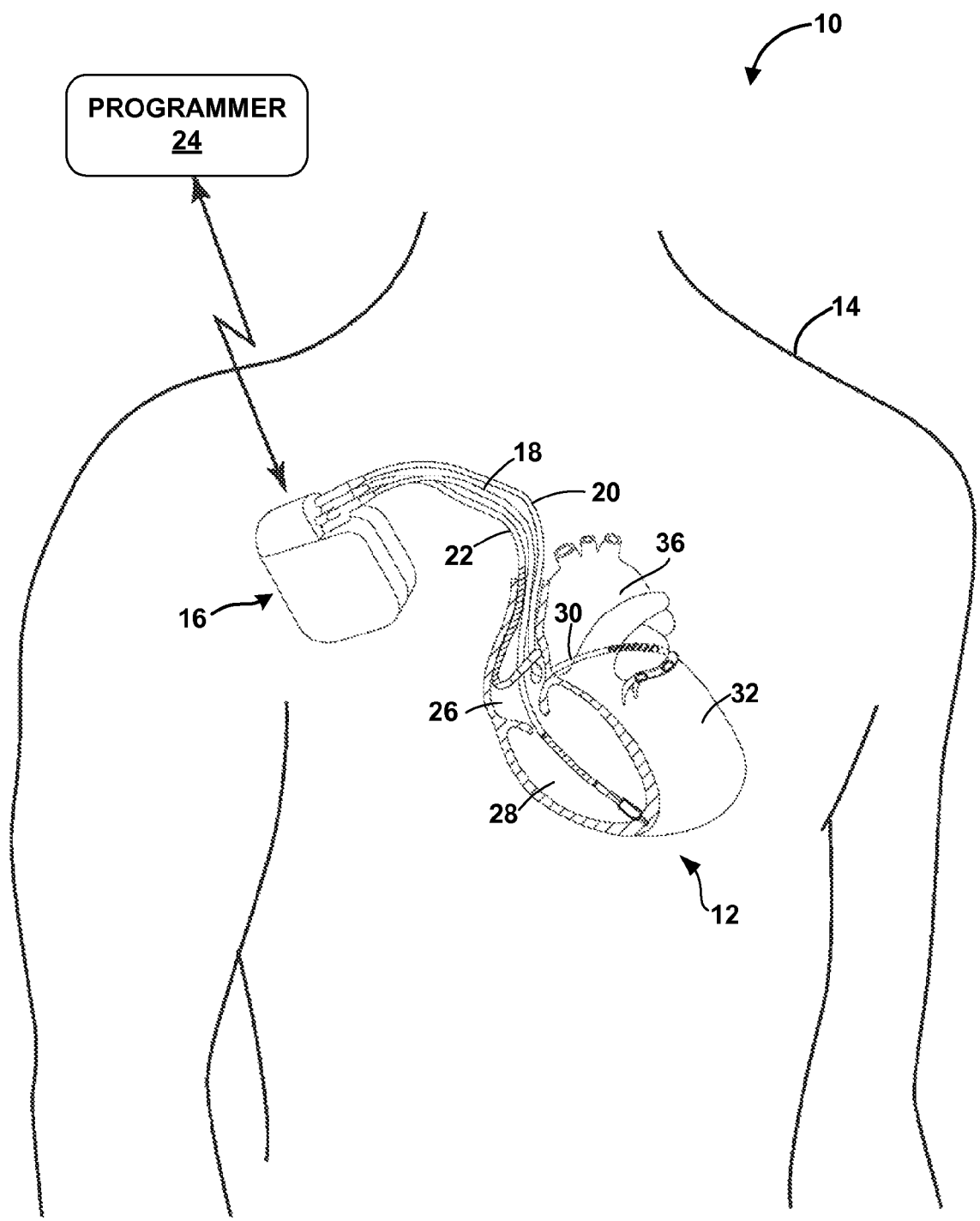
FIG. 1 is a conceptual diagram illustrating an example therapy system comprising an implantable medical device (IMD) for delivering stimulation therapy to a heart of a patient via implantable leads according to this disclosure.

In general, this disclosure is directed to techniques for configuring one or more components within an implantable medical device (IMD) such that effects on the IMD are controlled and/or reduced when the device is subject to a disruptive energy field. In some examples, the disruptive energy field may be a magnetic or radio frequency (RF) field generated by an electromagnetic energy source. In additional examples, the disruptive energy field may be an energy field produced by a medical imaging modality, such as a magnetic resonance imaging (MRI) modality for example. The energy from the electromagnetic energy source may induce current flow within electrical components of the lead, which can produce lead heating, RF rectification, device heating and other effects. As used herein, the terms "lead heating" or "lead heating effects" may refer to the heating of tissue proximate to one or more electrodes coupled to an implantable medical device.

Certain components within the IMD, although not primarily considered as inductive and/or capacitive components for conventional implantable device design, may nevertheless produce parasitic inductances and/or capacitances. The parasitic inductances and/or capacitances of such components may be utilized to deliberately design an electrical network that reduces the amount of electromagnetic energy reflected along a lead by the IMD for a given frequency or range of frequencies, and thereby reduce the effects caused by the disruptive energy field such as, e.g., lead heating, device rectification, or device heating.

When an IMD is placed within the presence of a disruptive energy field, the electromagnetic waves and/or energy associated with the field may propagate along the length of a lead towards the housing of the IMD. The electrical components within the device housing may reflect a substantial portion of the electromagnetic wave along the lead toward the electrodes. In some cases, the reflected electromagnetic wave may produce lead heating effects, e.g., tissue heating proximate to the electrodes. Because the techniques described in this disclosure may help to reduce the amount of reflected energy in the implanted lead, the techniques of this disclosure may be used to control the lead heating effects caused by placing the device in the presence of disruptive energy field.

The electromagnetic energy source may produce electromagnetic energy at any frequency. In examples where the electromagnetic energy source is an MRI modality, the electromagnetic energy source may, in some examples, produce electromagnetic waves or energy (e.g., a disruptive energy field) having frequencies of 42 MHz, 64 MHz, and/or 128 MHz. The proportion of 42 MHz radio frequency (RF) to a 1 Tesla (T) static magnetic field is controlled by the Larmar frequency. Therefore 42 MHz, 64 MHz, and 128 MHz correspond to 1 T, 1.5 T, and 3 T MRIs respectively. However, the techniques in this disclosure may be applied to other frequencies of MRIs as well.

In some examples, an IMD in accordance with this disclosure may have components selected such that an amount of reflected energy along a device lead is below a selected threshold. For example, the IMD may include an implantable lead that carries one or more electrodes, a first component having a parasitic inductance, and a second component having a reactance. In some examples, the reactance of the second component may be selected based on the parasitic inductance of the first component such that an amount of energy reflected along the lead in response to energy produced by an electromagnetic energy source is below a selected threshold. In additional examples, the parasitic inductance of the first component and the reactance of the second component are configured such that an amount of energy reflected along the lead in response to a frequency of energy emitted by the electromagnetic energy source is below the selected threshold.

In some examples, the amount of energy reflected along the lead (i.e., reflected energy) may refer to a raw amount of reflected energy. As used herein, a raw amount of reflected energy may refer to the magnitude of electromagnetic energy that is reflected at the proximal end of the lead (e.g., at the lead-device interface) in response to electromagnetic energy being induced in the lead by a disruptive electromagnetic field. In some examples, the raw amount of reflected energy may be an electromagnetic wave that travels towards the distal end of the lead (i.e., away from the lead-device interface).

In additional examples, the amount of energy reflected along the lead (i.e., reflected energy) may refer to a composite amount of reflected energy. As used herein, a composite amount of reflected energy may refer to the combination (e.g., superposition) of the raw amount of reflected energy along the lead and additional amounts of energy traveling along the respective lead. The additional amounts of energy may include energy that is reflected by the implantable medical device and/or energy that is not reflected by the implantable medical device. In some examples, the additional amounts of energy may include energy that is induced in the respective electrical lead by a disruptive electromagnetic energy field.

For example, when an implantable medical device is subject to a disruptive electromagnetic energy field, the disruptive electromagnetic energy field may induce a first type of electromagnetic wave in a lead coupled to the implantable medical device. The first type of electromagnetic wave may travel along the lead towards the proximal end of the lead (i.e., towards the lead-device interface of the implantable medical device). The disruptive electromagnetic energy field may also induce a second type of electromagnetic wave in the lead. The second type of electromagnetic wave may travel along the lead towards the distal end of the lead (i.e., away from the lead-device interface of the implantable medical device).

The implantable medical device may reflect the first type of electromagnetic wave to produce a third type of electromagnetic wave. For example, an electrical network formed by components of the implantable medical device, as described in further detail in this disclosure, may reflect the first type of electromagnetic wave and produce the third type of electromagnetic wave. The third type of electromagnetic wave may travel along the lead towards the distal end of the lead (i.e., away from the lead-device interface of the implantable medical device). The second type of electromagnetic wave and the third type of electromagnetic may combine (e.g., superpose) to form a composite amount of reflected energy. Thus, in such examples, the composite amount of reflected energy may refer to the combination (e.g., superposition) of the second type of electromagnetic wave and the third type of electromagnetic wave. The techniques in this disclosure may, in some examples, be used to cause the composite amount of energy reflected along the lead in response to energy produced by an electromagnetic energy source to be below a selected threshold.

In additional examples, an IMD in accordance with this disclosure may have components selected such that one or more of the following constraints are satisfied: (1) an amount of reflected energy along a device lead is below a first threshold; (2) an amount of energy transferred to active circuitry within the medical device is below a second threshold; and/or (3) an amount of energy dissipated by an electrical network within the IMD is below a third threshold. Again, as used in this disclosure, the term "reflected energy" may refer to a raw amount of reflected energy or a composite amount of reflected energy.

In some examples, an IMD in accordance with this disclosure may have components selected such that an electrical network that includes the components has a resonant frequency proximate to the frequency of energy produced by the electromagnetic energy source. In additional examples, an IMD in accordance with this disclosure may have components configured such that a magnitude of the resonance is within a particular range. In further examples, an IMD in accordance with this disclosure may have components configured such that the quality factor (Q-factor) or bandwidth of the electrical network is greater than a selected threshold.

As used herein, a parasitic inductance refers to internal inductance of a component whose primary function is something other than behaving as an inductor. In other words, the parasitic inductance is incidental to the primary function of the component. Similarly, a parasitic resistance refers to internal resistance of a component whose primary function is something other than behaving as a resistor. Likewise, a parasitic capacitance refers to the internal capacitance of a component whose primary function is something other than behaving as a capacitor.

In contrast, an actual inductance may refer to the inductance of a component whose primary function is to behave as an inductor. Similarly, an actual resistance may refer to the resistance of a component whose primary function is to behave as a resistor. Likewise, an actual capacitance may refer to the capacitance of a component whose primary function is to behave as a capacitor. Any determination of whether an inductance, resistance, or capacitance is parasitic or actual may be based upon the context and function of the components within a given circuit.

For purposes of illustration, the techniques of this disclosure will be described with respect to a disruptive energy field generated by an imaging modality and, more specifically, a magnetic resonance imaging (MRI) modality. The techniques of this disclosure may, however, be used in the context of other disruptive energy fields generated by imaging modalities other than MRI modalities or non-imaging medical or non-medical devices that generate an energy field.

Although the techniques in this disclosure are described with respect to "energy" or "an amount of energy," it should be recognized that other measures of electromagnetic fields and/or radiation may also be used. For example, "power" or "an amount of power" may be used in place of "energy" and/or "an amount of energy." In addition, where this disclosure refers to "electromagnetic waves," the disclosure may also be referring to "electromagnetic energy" and/or "electromagnetic radiation."

FIG. 1 is a conceptual diagram illustrating an example therapy system 10 that may be used to provide therapy to heart 12 of patient 14. Patient 14 is ordinarily, but not necessarily, a human patient. Therapy system 10 includes IMD 16, which is coupled to leads 18, 20, and 22, and programmer 24. Although leads 18, 20, 22 are described in FIG. 1 as being separate from IMD 16, in some examples, IMD 16 may include leads 18, 20, 22.

IMD 16 may be, for example, a device that provides cardiac rhythm management therapy to heart 12, and may include, for example, an implantable pacemaker, cardioverter, and/or defibrillator that provides therapy to heart 12 of patient 14 via electrodes coupled to one or more of leads 18, 20, and 22. In some examples, IMD 16 may deliver pacing pulses, but not cardioversion or defibrillation shocks, while in other examples, IMD 16 may deliver cardioversion and/or defibrillation shocks in addition to pacing pulses. In additional examples, IMD 16 may provide cardiac resynchronization therapy in addition to or in lieu of pacing pulses, cardioversion shocks, and/or defibrillation shocks.

Although the techniques in this disclosure are described with respect to an implantable cardiac device for exemplary purposes, such techniques may also be applied to other types of IMDs. For example, the techniques in this disclosure may be applied to neurostimulators, including deep brain stimulators, spinal cord stimulators, peripheral nerve stimulators, pelvic floor stimulators, gastro-intestinal stimulators, or the like.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In other examples, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 senses electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. These electrical signals sensed within heart 12 may also be referred to as cardiac signals or electrical cardiac signals. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver cardioversion or defibrillation therapy to heart 12 in the form of electrical pulses. In some examples, IMD 16 may be programmed to deliver a progression of therapies, e.g., pulses with increasing energy levels, until a tachyarrhythmia of heart 12 is stopped. IMD 16 detects tachycardia or fibrillation employing one or more tachycardia or fibrillation detection techniques known in the art.

In some examples, programmer 24 may be a handheld computing device, computer workstation, or networked computing device. Programmer 24 includes a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 or IMD 16 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as electrical depolarization/repolarization signals from the heart (referred to as "electrogram" or EGM), intracardiac or intravascular pressure, activity, posture, respiration, heart rate, heart sounds, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation shocks, select waveforms for the defibrillation shocks, or select or configure a fibrillation detection algorithm for IMD 16. The user may also use programmer 24 to program similar aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In accordance with this disclosure, IMD 16 may have one or more components configured such that, when patient 14 and/or IMD 16 are in the presence of an electromagnetic energy source, the amount of energy reflected by IMD 16 is less than a selected threshold. In some examples, the reactance of a reactive component within IMD 16 may be selected based on a parasitic inductance of another component within IMD 16 in order to control the amount of energy reflected by IMD 16. For example, a capacitance for a channel capacitor within IMD 16 may be selected based on a parasitic inductance of ribbon bonding and/or conductive traces within IMD 16.

Each lead 18, 20, 22 may include one or more electrical conductors. Each conductor may extend between an electrical contact at a proximal end of a lead and an electrode at a distal end of the lead. The conductors may conduct stimulation current to the electrodes and/or conduct sensing current from the electrodes. The electrical contacts may be electrically coupled to respective electrical terminals in a header associated with the housing of the IMD 16. The ribbon bonding and/or conductive traces may electrically couple the electrical terminals to corresponding electrical terminals inside the housing of the IMD 16, e.g., on a circuit board that includes various electronic circuit components for generation, control and/or processing of electrical stimulation and/or sensing signals. The conductors may carry current that is induced by energy associated with an electromagnetic energy source, such as an MRI or other imaging modality.

In additional examples, a parasitic inductance value for a first component and a reactance for a second component may be selected and configured in order to control the amount of energy reflected by IMD 16 along the length of leads 18, 20, 22 toward the electrodes at the distal ends of the leads. For example, the length of ribbon bonding and/or conductive traces within IMD 16 may be adjusted to control the parasitic inductance of the first component. In addition, a capacitance value may be selected for a channel capacitor within IMD 16 to control the reactance of the second component. The first component and the second component may operate together to produce a resonance proximate to the frequency of the electromagnetic energy source.

In some cases, the length of the ribbon bonding and/or conductive traces can be selected based on a fixed capacitance value of the channel capacitor to produce a resonance at a desired frequency. In some examples, the fixed capacitance value may be based on one or more standard capacitance values for channel capacitors used in a particular manufacturing process for an IMD or circuit board. Alternatively, the capacitance value of the channel capacitor may be selected based on a fixed inductance value of the ribbon bonding and/or conductive traces to produce a resonance at a desired frequency. In some examples, the fixed inductance value may be based on a parasitic inductance value associated with a particular configuration (e.g., length) of ribbon bonding and/or conductive traces used in a particular manufacturing process for an IMD or circuit board. As a further alternative, the capacitance of the channel capacitor and the length of the ribbon bonding and/or conductive traces may both be adjusted or selected to produce a resonance at a desired frequency.

In some examples, the first and second components may be configured such that a magnitude of the resonance is within a particular range. In further examples, the first and second components may be configured such that the quality factor (Q-factor) or bandwidth of an electrical network containing the first and second components is greater than a selected threshold.

In further examples, IMD 16 may have components selected such that one or more of the following constraints are satisfied: (1) an amount of reflected energy along a device lead is below a first threshold; (2) an amount of energy transferred to active circuitry within the medical device is below a second threshold; and/or (3) an amount of energy dissipated by an electrical network within the IMD is below a third threshold.

Figure 2:
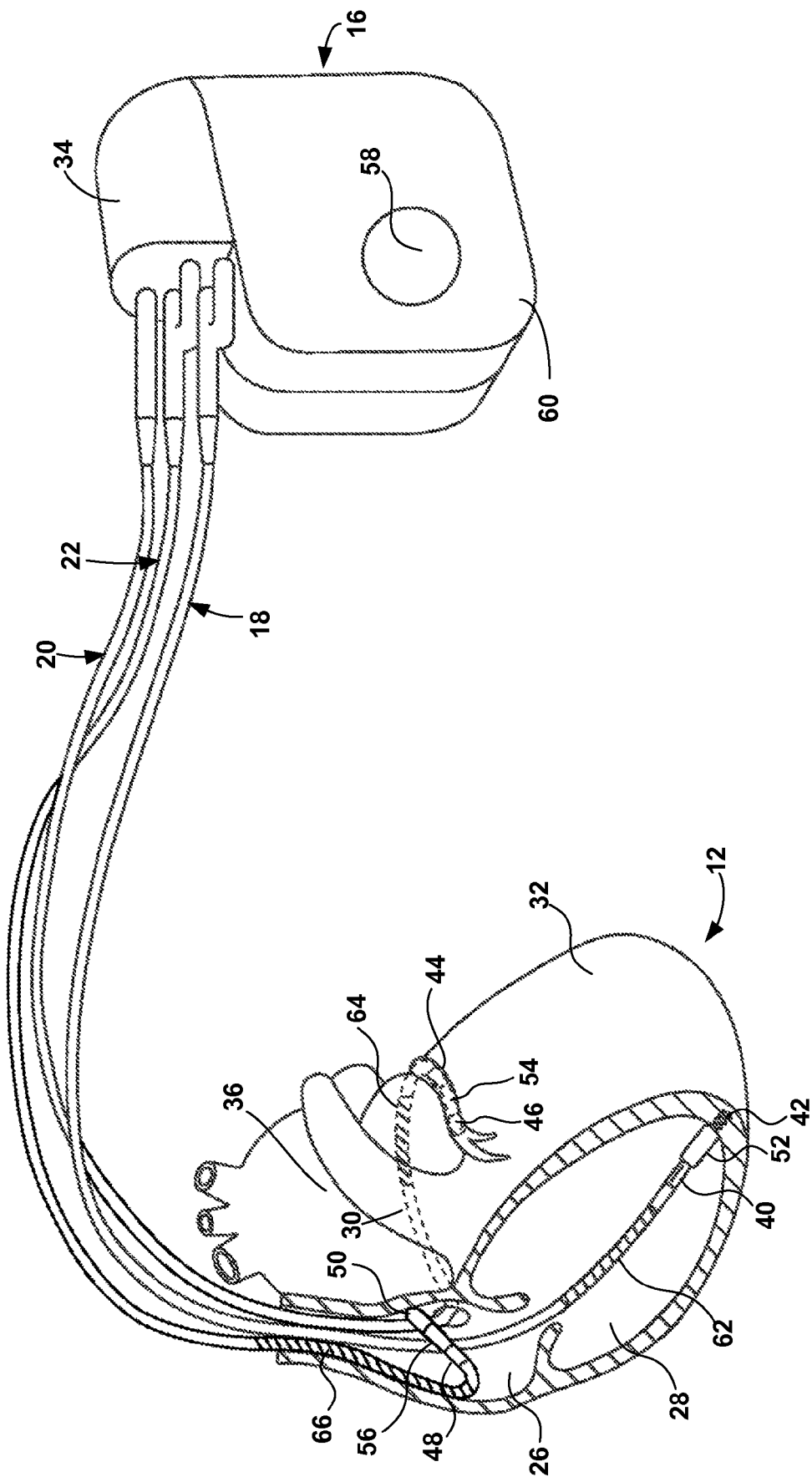
FIG. 2 is a conceptual diagram further illustrating the IMD and leads of the system of FIG. 1 in greater detail.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 40 and 42 are located proximate to a distal end of lead 18 in RV 28. In addition, bipolar electrodes 44 and 46 are located proximate to a distal end of lead 20 in LV 32 and bipolar electrodes 48 and 50 are located proximate to a distal end of lead 22 in RA 26. Although no electrodes are located in LA 36 in the illustrated example, other examples may include electrodes in LA 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other divisions between insulated and uninsulated portions of housing 60 may be employed to define two or more housing electrodes. In some examples, housing electrode 58 comprises substantially all of housing 60. As described in further detail with reference to FIGS. 3 and 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some examples may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode in the may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation shocks to heart 12 via any combination of elongated electrodes 62, 64, 66, and housing electrode 58. Electrodes 58, 62, 64, 66 may also be used to deliver cardioversion shocks to heart 12. Electrodes 62, 64, 66 may be fabricated from any suitable electrically conductive material, such as, but not limited to, platinum, platinum alloy, Titanium nitride or other materials known to be usable in implantable defibrillation electrodes.

As described above, exposure of IMD 16 to a disruptive energy field, e.g., one or more fields produced by an MRI imaging modality, may result in lead heating, RF rectification, device heating, and/or other effects. For example, RF fields produced by the MRI imaging modality may induce energy on one or more conductors of respective ones of implantable leads 18, 20, or 22 or on the housing electrode, which may in turn increase lead heating, device rectification, and/or device heating effects. According to this disclosure, techniques for configuring one or more electrical components within IMD 16 are provided that may reduce and/or control one or more of such effects.

The configuration of therapy system 10 illustrated in FIGS. 1 and 2 is merely one example. In other examples, a therapy system may include epicardial leads and/or patch electrodes instead of or in addition to the implanted leads 18, 20, 22 illustrated in FIG. 1. Further, housing 60 of IMD 16 need not be implanted within patient 14. In examples in which housing 60 is not implanted in patient 14, IMD 16 may deliver defibrillation pulses and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, a therapy system may include a single chamber or dual chamber device rather than a three-chamber device as shown in FIG. 1. In a single chamber configuration, IMD 16 is electrically connected to a single lead 20 that includes stimulation and sense electrodes within LV 32. In one example of a dual chamber configuration, IMD 16 is electrically connected to a single lead that includes stimulation and sense electrodes within LV 32 as well as sense and/or stimulation electrodes within RA 26. In another example of a dual chamber configuration, IMD 16 is connected to two leads that extend into a respective one of the RA 28 and LV 32. Other lead configurations are contemplated, and the techniques in this disclosure are not limited to any particular number of leads or configuration of leads.

The techniques of this disclosure may be used to operate an IMD that provides other types of electrical stimulation therapy other than cardiac rhythm management therapy or in devices that provide no therapy at all, but only monitor a condition of a patient. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
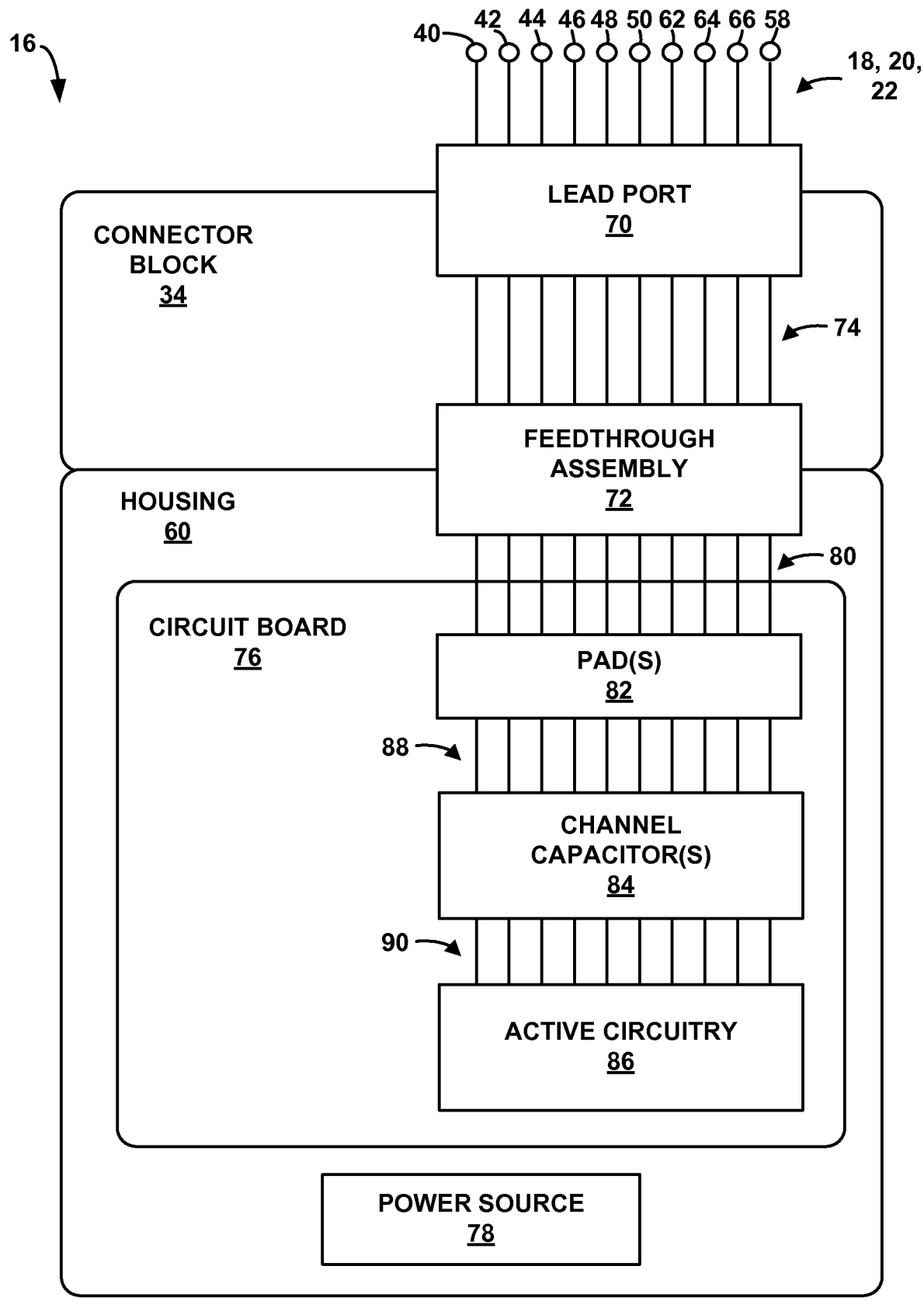
FIG. 3 is a block diagram illustrating an example configuration of an IMD according to this disclosure.

FIG. 3 is a block diagram illustrating an example configuration of IMD 16. In the example illustrated by FIG. 3, IMD 16 includes connector block 34 and housing 60. Connector block 34 is configured to couple leads 18, 20, 22 to IMD 16. Connector block 34 includes lead port 70, feedthrough assembly 72 and conductors 74.

Lead port 70 may be configured to secure leads 18, 20, 22 to connector block 34. Each of leads 18, 20, 22 may have a lead connector on the proximal end of the lead, which can be inserted into lead port 70. The proximal lead connector may include electrical contacts, each of which may be coupled to a respective electrode at the distal end of the lead via a respective lead conductor. Lead port 70 may include a suitable means for locking the lead connector into lead port 70 such that, when inserted, each of the electrical contacts is electrically coupled to a respective conductor 74. For example, lead port 70 may include one or more lead receptacles each of which are configured to receive and lock one of leads 18, 20, 22 in place.

Feedthrough assembly 72 is configured to provide electrical communication between the outside and inside of hermetically-sealed housing 60. Feedthrough assembly may, in some examples, be affixed to a side-wall of housing 60. Feedthrough assembly 72 may include any type of conductor that provides a conductive pathway between the exterior and interior of housing 60. Each of the feedthrough conductors may have a first terminal that is disposed outside of housing 60 and a second terminal that is disposed inside of housing 60. The first terminal of each feedthrough conductor may be electrically coupled to respective conductor 74, which is in turn electrically coupled to a respective lead 18, 20, 22. A second terminal of each feedthrough conductor may be electrically coupled to a respective pad 82 on circuit board 76. In some examples, the feedthrough conductors may include one or more feedthrough pins.

Feedthrough assembly 72 may, in some examples, include one or more feedthrough capacitors. For each feedthrough capacitor, a first terminal may be electrically coupled to a portion of a respective feedthrough conductor (e.g., the feedthrough pin) and a second terminal may be electrically coupled to housing 60. In addition, the first terminal of the feedthrough capacitor may be electrically coupled to a respective contact of an implantable lead, e.g., via a respective conductor 74. The feedthrough capacitors may be configured to block or attenuate electromagnetic interference (EMI) from entering housing 60 and electronic circuitry of IMD 16. In some examples, the feedthrough capacitors may attenuate any incoming high frequency electrical energy, e.g., any frequency of electrical energy that is above approximately 3 MHz. Although the feedthrough capacitors are described as being included within feedthrough assembly 72, in other examples, the feedthrough capacitors may be completely or partially outside of feedthrough assembly 72.

EMI (e.g., a disruptive energy field) may refer to any unwanted electrical noise (e.g., energy). In other words, EMI may include any electromagnetic signal or noise detected by leads 40, 42, 44, 46, 48, 50, 58, 62, 64, 66 other than the physiological signals which the leads are designed to detect. For example, EMI may include electromagnetic interference due to cell phones, microwaves, radios, radar, television, monitors, spark plugs, electric motors, or any other device operated near IMD 16 that produces electromagnetic energy.

Each of the feedthrough capacitors contained within feedthrough assembly 72 may have a capacitance value associated with the capacitor. As described in further detail in this disclosure, the capacitance values for each of the feedthrough capacitors may be selected and/or adjusted based on parasitic inductances contained with IMD 16 to control and/or reduce lead heating effects, RF rectification, and/or device heating effects caused by a disruptive energy field.

Conductors 74 are configured to provide electrical communication between lead port 70 and feedthrough assembly 72. In some examples, each conductor 74 may be associated with a respective electrical contact in lead port 70 and a respective feedthrough conductor and/or feedthrough capacitor in feedthrough assembly 72. Thus, for each of the conductors 74, a first end or terminal may be electrically coupled to a respective electrical contact within lead port 70 and a second end or terminal electrically coupled to a feedthrough conductor contained in feedthrough assembly 72. In some examples, each of the conductors 74 may be implemented as a conductive wire or as an interconnect ribbon.

Housing 60 may be configured to shield the electrical components contained inside of housing 60 from body fluids of patient 14 and from EMI. As described in further detail in this disclosure, electrical components that are partially and/or completely contained within housing 60 may be configured such that an amount of energy reflected by IMD 16 in response to energy emitted by an electromagnetic energy source is less than a selected threshold.

In some examples, the reactance of a reactive component may be configured based on the parasitic inductance of another component. In additional examples, the reactance of one component and the parasitic inductance of another component may be configured such that an electrical network containing the components resonates at a particular frequency. The resonant frequency may be a frequency that is near (i.e., proximate) to a frequency of electromagnetic energy produced by an electromagnetic energy source such that lead heating effects associated with the electromagnetic energy source are reduced. For example, the resonant frequency may be proximate to a frequency of electromagnetic energy produced by an MRI or other medical imaging modality. In some examples, the frequency of the electromagnetic energy may be a center frequency of the electromagnetic energy produced by the electromagnetic energy source.

As the distance between the resonant frequency and the frequency of electromagnetic energy produced by the electromagnetic energy source decreases, the amount of electrical energy reflected along the length of a lead by the electrical network may also decrease. Thus, by configuring the electrical network to resonate a frequency proximate to the frequency of electromagnetic energy, the amount of current within the lead may be reduced thereby reducing lead heating effects.

As illustrated in FIG. 3, housing 60 includes feedthrough assembly 72, circuit board 76, power source 78, and ribbon bonds 80. Circuit board 76 may be a substrate that is used to mechanically support and electrically connect electrical components contained on circuit board 76. In some examples, circuit board 76 may be a printed circuit board (PCB) or a printed wiring board (PWB). Circuit board 76 may be electrically coupled to feedthrough assembly 72 via ribbon bonds 80. In addition, circuit board 76 may be electrically coupled to power source 78. Circuit board 76 may include one or more pads 82, one or more channel capacitors 84, active circuitry 86, and one or more conductive traces 88, 90. In some examples, one or more of these components may be affixed to circuit board 76.

Ribbon bonds 80 are configured to provide electrical communication between feedthrough assembly 72 and circuit board 76. Each of ribbon bonds 80 may have a first end or terminal that is electrically coupled to a respective feedthrough conductor within feedthrough assembly 72, and a second end or terminal that is electrically coupled to a respective pad 82 on printed circuit board 76. In some examples, one or more of the ribbon bonds 80 may include a laser ribbon bond that is laser-welded to a feedthrough pin at a first end and to a contact pad 82 at a second end.

Although ribbon bonds 80 are primarily intended to serve as electrical conductors for delivery of electrical current to and from electrodes on the leads, each of the ribbon bonds 80 may have a parasitic inductance associated with the ribbon bond. As described in further detail in this disclosure, these parasitic inductances may be utilized in conjunction with other reactive components to control effects (e.g. lead heating effects, RF rectification effects, device heating effects, etc.) that occur within IMD 16 and leads 18, 20, 22 due to a disruptive energy field, such as a medical imaging modality.

Pads 82 (e.g., contact pads) are configured to receive an electrical signal from a component not affixed to circuit board 76 and to relay the electrical signal to other components affixed to circuit board 76. For each pad, a first terminal may be electrically coupled to a respective feedthrough conductor in feedthrough assembly 72 via a respective ribbon bond 80, and a second terminal may be electrically coupled to a respective channel capacitor 84 via a respective conductive trace 88. Thus, pads 82 operate as an interface between off-board and on-board electrical components.

Channel capacitors 84 may be configured to route stray high-frequency signals and telemetry signals to a ground voltage terminal (not shown) of circuit board 76. For each channel capacitor 84, a first terminal may be electrically coupled to a respective conductive trace 88 and a respective conductive trace 90, and a second terminal may be electrically coupled to a ground voltage terminal of circuit board 76. Each channel capacitor 84 may have a capacitance value associated with the capacitor. The capacitance value may be selected and/or adjusted based on parasitic inductances contained with IMD 16 to produce, in combination with other reactive components, a resonant frequency that serves to control and/or reduce effects caused by a disruptive energy field.

Active circuitry 86 is configured to control therapy and measurement operations of IMD 16. Active circuitry 86 may also include any other components or sub-circuits typically included within an IMD. As described in further detail with respect to FIG. 4, active circuitry may include a diode protection array that protects the active circuitry components. Active circuitry 86 may be electrically coupled to channel capacitors 84 via conductive traces 90.

Conductive traces 88, 90 are configured to interconnect various electrical components within circuit board 76. In some examples, circuit board 76 may comprise a non-conductive substrate, and the conductive traces 88, 90 may be formed by etching conductive copper sheets that are laminated on the non-conductive substrate. Conductive traces 88 may include one or more conductive traces, each of which has a first portion or terminal that is electrically coupled to a respective pad 82 and a second portion or terminal that is electrically coupled to a respective channel capacitor 84. Conductive traces 90 may include one or more conductive traces, each of which has a first portion or terminal that is electrically coupled to a respective channel capacitors 84 and a second portion or terminal that is electrically coupled to a respective terminal of active circuitry 86

In some examples, the terminal of active circuitry 84 may be a first terminal of a diode within active circuitry, and the second terminal of the diode may be electrically coupled to a ground terminal of circuit board 76. Each of the conductive traces 88, 90 may have a parasitic inductance associated with the trace. As described in further detail in this disclosure, these parasitic inductances may be utilized in conjunction with other reactive components to control and/or reduce lead heating effects due to an electromagnetic energy source that produces EMI.

As used herein, a component of IMD 16 may refer to any electrical component within IMD 16 including conductors 74, channel capacitors 84, active circuitry 86, conductive traces 88, 90, feedthrough capacitors contained within feedthrough assembly 72, or any other electrical component that is partially or completely contained within housing 60, any component that is partially or completely contained within connector block 34 of IMD 16, or any component that is electrically coupled to IMD 16.

IMD 16 may include a plurality of channels, each of which may be associated with a respective electrode 40, 42, 44, 46, 48, 50, 58, 62, 64, 66. In other words, each channel within IMD 16 may be associated with a conductive pathway that provides electrical communication between a terminal within IMD 16 and a respective electrode 40, 42, 44, 46, 48, 50, 58, 62, 64, 66. As described above with respect to FIG. 3, each conductive pathway may have a respective conductor 74, a respective feedthrough conductor within feedthrough assembly 72, a respective feedthrough capacitor, a respective ribbon bond 80, a respective pad 82, a respective conductive trace 88, a respective channel capacitor 84, a respective conductive trace 90, and a respective terminal of active circuitry 86.

Power source 78 is configured to supply power to one or more of the components within IMD 16. Power source 78 may include a rechargeable or non-rechargeable battery. A non-rechargeable battery may be capable of holding a charge for several years, while a rechargeable battery may be inductively charged from an external device, e.g., on a daily or weekly basis. Examples of a rechargeable battery include, but are not limited to, a lithium ion battery, a lithium polymer battery or a supercapacitor. Each of the components within IMD 16 may be electrically coupled to power source 78.

Figure 4:
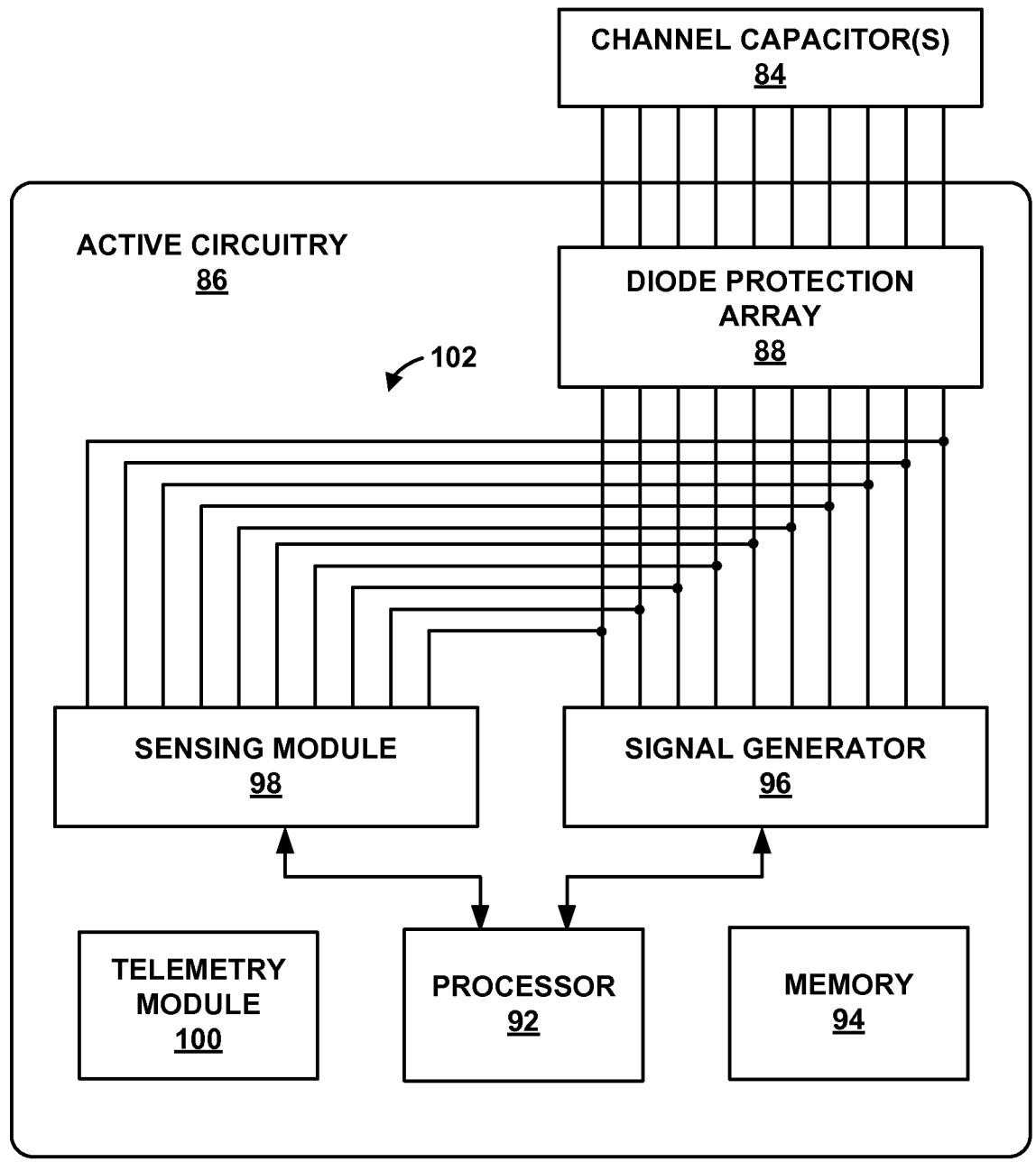
FIG. 4 is a block diagram illustrating active circuitry of FIG. 3 in greater detail.

FIG. 4 is a block diagram illustrating the active circuitry 86 of FIG. 4 in greater detail. Active circuitry 86 may include diode protection array 88, processor 92, memory 94, signal generator 96, electrical sensing module 98, telemetry module 100, and conductive traces 102.

Diode protection array 88 may be configured to prevent excess voltage from entering components within active circuitry 96. Diode protection array 88 may include one or more diodes. Each of the diodes may have a first terminal that is electrically coupled to a respective terminal of signal generator 96 and a corresponding respective terminal of sensing module 98 via a respective conductive trace 102. The first terminal of each diode may also be electrically coupled to a respective channel capacitor 84. Each of the diodes within diode protection array 88 may have a second terminal electrically coupled to a ground voltage of circuit board 76. The one or more diodes within diode protection array 88 may be any combination of forward-biased diodes and/or reversed-biased diodes. In some examples, each channel may include a single diode, such as a zener diode for example. In other examples, each channel may include a plurality of diodes.

In cases where a high-frequency signal reaches diode protection array 88 via conductive traces 90, rather than preventing excess voltage from entering components, the diodes may produce a rectified version of the high-frequency signal that is transferred to active circuitry 86. This phenomenon may be referred to as "radio frequency (RF) rectification." According to the techniques in this disclosure, the amount of RF rectification that occurs when IMD 16 is subject to a disruptive energy field may be controlled. For example, the components within IMD 16 may be configured such that the amount of energy reflected along the lead in response to energy emitted by an electromagnetic energy source is less than a first threshold, and the amount of energy transferred to the active circuitry is below a second threshold. For example, an effective resistance (e.g., real impedance) of an electrical network that includes channel capacitors 84, ribbon bond 80 and/or conductive traces 88, 90 may be increased to increase the amount of energy dissipated by the electrical network. By increasing the effective resistance of the electrical network, lead heating effects due to an EMI produced by an electromagnetic energy source may be reduced without causing a prohibitive increase in the amount of RF rectification.

As described above with respect to FIG. 3, each channel within IMD 16 may be associated with a conductive pathway that includes a respective conductor 74, a respective feedthrough conductor within feedthrough assembly 72, a respective feedthrough capacitor, a respective ribbon bond 80, a respective pad 82, a respective conductive trace 88, a respective channel capacitor 84, a respective conductive trace 90, and a respective terminal of active circuitry 86. In addition, the conductive pathway may also include a respective terminal within diode protection array 88, a respective set of one or more diodes within diode protection array 88, a respective terminal within signal generator 96, and a respective terminal within sensing module 98. Thus, each channel within IMD 16 may be associated with or comprise a conductive pathway from an individual electrode 40, 42, 44, 46, 48, 50, 58, 62, 64, 66 to a respective terminal of diode protection array 88, signal generator 96, and/or sensing module 98.

Processor 92 may include any one or more of a microprocessor, a controller, a digital signal processor (DSP), an application specific integrated circuit (ASIC), a field-programmable gate array (FPGA), or equivalent discrete or integrated logic circuitry. In some examples, processor 92 may include multiple components, such as any combination of one or more microprocessors, one or more controllers, one or more DSPs, one or more ASICs, or one or more FPGAs, as well as other discrete or integrated logic circuitry. The functions attributed to processor 92 herein may be embodied as software, firmware, hardware or any combination thereof.

Processor 92 controls signal generator 96 to deliver stimulation therapy to heart 12. Processor 92 may control signal generator 96 to deliver stimulation according to a selected one or more therapy programs, which may be stored in memory 94. For example, processor 92 may control signal generator 96 to deliver electrical pulses with the amplitudes, pulse widths, frequencies, or electrode polarities specified by the selected one or more therapy programs.

Memory 94 may include computer-readable instructions that, when executed by processor 92, cause IMD 16 and processor 92 to perform various functions attributed to IMD 16 and processor 92 herein. Memory 94 may include any volatile, non-volatile, magnetic, optical, or electrical media, such as a random access memory (RAM), read-only memory (ROM), non-volatile RAM (NVRAM), static RAM (SRAM), electrically-erasable programmable ROM (EEPROM), flash memory, or any other digital media.

Signal generator 96 is configured to generate and deliver electrical stimulation therapy to heart 12. Signal generator 96 may deliver pacing pulses via ring electrodes 40, 44, 48 coupled to leads 18, 20, and 22, respectively, and/or helical electrodes 42, 46, and 50 of leads 18, 20, and 22, respectively. For example, signal generator 96 may deliver a pacing stimulus to LV 32 (FIG. 2) of heart 12 via at least two electrodes 44, 46 (FIG. 2). As another example, signal generator 96 may deliver defibrillation shocks to heart 12 via at least two electrodes 58, 62, 64, 66. In some examples, signal generator 96 delivers pacing, cardioversion, or defibrillation stimulation in the form of electrical pulses. In other examples, signal generator 96 may deliver one or more of these types of stimulation in the form of other signals, such as sine waves, square waves, or other substantially continuous time signals.

In some examples, signal generator 96 may include a switch module and processor 92 may use the switch module to select, e.g., via a data/address bus, which of the available electrodes are used to deliver pacing pulses, cardioversion shocks, or defibrillation shocks. The switch module may include a switch array, switch matrix, multiplexer, or any other type of switching device suitable to selectively couple stimulation energy to selected electrodes. In other examples, however, signal generator 96 may independently deliver stimulation to electrodes 40, 42, 44, 46, 48, 50, 58, 62, 64, 66 or selectively sense via one or more of electrodes 40, 42, 44, 46, 48, 50, 58, 62, 64, 66 without a switch matrix.

Signal generator 96 may include a plurality of terminals, each of which is electrically coupled to a first terminal of a respective diode within diode protection array 88. The second terminal of each of the diodes may be electrically coupled to a ground voltage terminal of circuit board 76. Since the diode protection array is electrically coupled to feedthrough assembly 72 and lead port 70, each of the terminals of signal generator may be electrically coupled to a respective one of electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16.

Sensing module 98 is configured to monitor signals from at least one of electrodes 40, 42, 44, 46, 48, 50, 58, 62, 64, 66 in order to monitor electrical activity of heart 12. For example, sensing module 98 may sense atrial events (e.g., a P-wave) with electrodes 48, 50, 66 within RA 26 or sense an LV 32 event (e.g., an R-wave) with electrodes 44, 46, 64 within LV 32. Sensing module 98 may also include a switch module to select which of the available electrodes are used to sense the heart activity. In some examples, processor 92 may select the electrodes that function as sense electrodes, or the sensing electrode configuration, via the switch module within electrical sensing module 98, e.g., by providing signals via a data/address bus. In some examples, sensing module 98 may include multiple sensing channels, each of which may comprise an amplifier. In response to the signals from processor 92, the switch module of within sensing module 98 may couple the outputs from the selected electrodes to one or more of the sensing channels.

In some examples, sensing module 98 may include a plurality of channels. One channel of sensing module 98 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, in one operating mode of sensing module 98, the R-wave amplifiers may take the form of an automatic gain controlled amplifier that provides an adjustable sensing threshold as a function of the measured R-wave amplitude of the heart rhythm.

In addition, in some examples, one channel of sensing module 98 may include a P-wave amplifier that receives signals from electrodes 48 and 50, which are used for pacing and sensing in right atrium 26 of heart 12. In some examples, in one operating mode of sensing module 98, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 98 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 98 may include a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 94 as an EGM. In some examples, the storage of such EGMs in memory 94 may be under the control of a direct memory access circuit. Processor 92 may employ digital signal analysis techniques to characterize the digitized signals stored in memory 94 to detect and classify the patient's heart rhythm from the electrical signals. Processor 92 may detect and classify the heart rhythm of patient 14 by employing any of the numerous signal processing methodologies known in the art.

In some examples, processor 92 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In some examples, processor 92 may include atrial and ventricular pacing escape intervals, refractory periods during which sensed P-waves and R-waves are ineffective to restart timing of the escape intervals, and the pulse widths of the pacing pulses. As another example, pacer timing and control module 92 may define a blanking period, and provide signals from sensing module 98 to blank one or more channels, e.g., amplifiers, for a period during and after delivery of electrical stimulation to heart 12. The durations of these intervals may be determined by processor 92 in response to stored data in memory 94. The pacer timing and control module of processor 92 may also determine the amplitude of the cardiac pacing pulses.

During pacing, escape interval counters within pacer timing and control module 92 of processor 92 may be reset upon sensing of R-waves and P-waves with detection channels of electrical sensing module 98. Signal generator 96 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 92 may reset the escape interval counters upon the generation of pacing pulses by signal generator 96, and thereby control the basic timing of cardiac pacing functions, including anti-tachyarrhythmia pacing.

The value of the count present in the escape interval counters when reset by sensed R-waves and P-waves may be used by processor 92 to measure the durations of R-R intervals, P-P intervals, P-R intervals and R-P intervals, which are measurements that may be stored in memory 94. Processor 92 may use the count in the interval counters to detect a tachyarrhythmia event, such as ventricular fibrillation event or ventricular tachycardia event. Upon detecting a threshold number of tachyarrhythmia events, processor 92 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processor 92 may operate as an interrupt driven device that is responsive to interrupts from pacer timing and control module 92, where the interrupts may correspond to the occurrences of sensed P-waves and R-waves and the generation of cardiac pacing pulses. Any necessary mathematical calculations to be performed by processor 92 and any updating of the values or intervals controlled by pacer timing and control module 92 of processor 92 may take place following such interrupts. A portion of memory 94 may be configured as a plurality of recirculating buffers, capable of holding a series of measured intervals, which may be analyzed by processor 92 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 92 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NON-LETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian, filed Jan. 8, 2004, are incorporated herein by reference in their entireties. However, other arrhythmia detection methodologies may also be employed by processor 92 in other examples.

In additional examples, processor 92 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 94 of IMD 16. In addition, the number of tachyarrhythmia events that are detected to confirm the presence of a tachyarrhythmia episode may be stored as a number of intervals to detect (NID) threshold value in memory 94. In some examples, processor 92 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 92 may determine that the tachyarrhythmia is present.

In the event that processor 92 detects an atrial or ventricular tachyarrhythmia based on signals from electrical sensing module 98, and an anti-tachyarrhythmia pacing regimen is desired, timing intervals for controlling the generation of anti-tachyarrhythmia pacing therapies by signal generator 96 may be loaded by processor 92 into pacer timing and control module 92 to control the operation of the escape interval counters therein and to define refractory periods during which detection of R-waves and P-waves is ineffective to restart the escape interval counters.

If IMD 16 is configured to generate and deliver defibrillation shocks to heart 12, signal generator 96 may include a high voltage charge circuit and a high voltage output circuit. In the event that generation of a cardioversion or defibrillation shock is required, processor 92 may employ the escape interval counter to control timing of such cardioversion and defibrillation shocks, as well as associated refractory periods. In response to the detection of atrial or ventricular fibrillation or tachyarrhythmia requiring a cardioversion pulse, processor 92 may activate a cardioversion/defibrillation control module, which may, like pacer timing and control module 92, be a hardware component of processor 92 and/or a firmware or software module executed by one or more hardware components of processor 92. The cardioversion/defibrillation control module may initiate charging of the high voltage capacitors of the high voltage charge circuit of signal generator 96 under control of a high voltage charging control line.

Processor 92 may monitor the voltage on the high voltage capacitor, e.g., via a voltage charging and potential (VCAP) line. In response to the voltage on the high voltage capacitor reaching a predetermined value set by processor 92, processor 92 may generate a logic signal that terminates charging. Thereafter, timing of the delivery of the defibrillation or cardioversion pulse by signal generator 96 is controlled by the cardioversion/defibrillation control module of processor 92. Following delivery of the fibrillation or tachycardia therapy, processor 92 may return signal generator 96 to a cardiac pacing function and await the next successive interrupt due to pacing or the occurrence of a sensed atrial or ventricular depolarization.

Signal generator 96 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of signal generator 96.

Telemetry module 100 is configured to receive downlink telemetry from and send uplink telemetry to programmer 24 with the aid of an antenna, which may be internal and/or external. Telemetry module 100 may be controlled by processor 92. Telemetry module 100 includes any suitable hardware, firmware, software or any combination thereof for communicating with another device, such as programmer 24 (FIG. 1). Processor 92 may provide the data to be uplinked to programmer 24 and the control signals for the telemetry circuit within telemetry module 100, e.g., via an address/data bus. In some examples, telemetry module 100 may provide received data to processor 92 via a multiplexer.

In some examples, processor 92 may transmit atrial and ventricular heart signals (e.g., EGM signals) produced by atrial and ventricular sense amp circuits within electrical sensing module 98 to programmer 24. Programmer 24 may interrogate IMD 16 to receive the EGMs. Processor 92 may store EGMs within memory 94, and retrieve stored EGMs from memory 94. Processor 92 may also generate and store marker codes indicative of different cardiac events that electrical sensing module 98 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Figure 5:
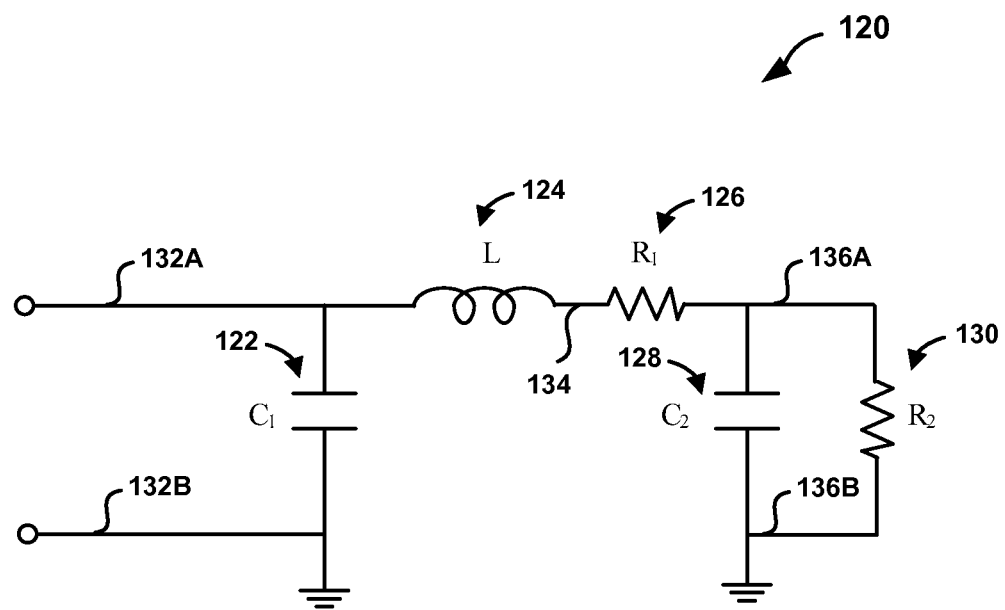
FIG. 5 is a circuit diagram illustrating an example electrical network that models electrical behavior of various components within an IMD according to this disclosure.

FIG. 5 is a circuit diagram illustrating an example electrical network 120 that models electrical behavior of various components within IMD 16. Electrical network 120 includes feedthrough capacitance 122, inductance 124, resistance 126, channel capacitance 128, resistance 130, input terminal nodes 132A, 132B, node 134, and output terminal nodes 136A, 136B.

In some examples, electrical network 120 may model electrical behavior for a particular channel within IMD 16. As already described above, a channel may be associated with a conductive pathway from a terminal within IMD 16 to a respective electrode 40, 42, 44, 46, 48, 50, 58, 62, 64, 66. Thus, each channel within IMD 16 may be modeled by an electrical network similar to electrical network 120 illustrated in FIG. 5. In some examples, each channel may include an identical electrical network. In other examples, the component values within the electrical networks may vary from channel-to-channel. For example, the component values for each channel may be selected based on the implanted location (e.g., region of the heart) of the associated electrode.

Input terminal node 132A may be electrically coupled to one or more of leads 18, 20, 22 and/or electrodes 40, 42, 44, 46, 48, 50, 58, 62, 64, and 66. In some examples, input terminal node 132 may be electrically coupled to a feedthrough pin in feedthrough assembly 72. Input terminal node 132B may be electrically coupled to housing 60 of IMD 16. Output terminal node 136A may be electrically coupled to active circuitry 86. Output terminal node 136B may be electrically coupled to a ground voltage terminal of circuit board 76. In some cases, output terminal node 136B may be capacitively coupled to input terminal node 132B.

Feedthrough capacitance 122 may correspond to the capacitance of one or more of the feedthrough capacitors located within feedthrough assembly 72. Feedthrough capacitance 122 has a capacitance value of $C_1$. Feedthrough capacitance 122 has a first terminal that is electrically coupled to input terminal 132A, and a second terminal that is electrically coupled to input terminal 132B.

Inductance 124 may correspond to the parasitic and/or actual inductance of one or more electrical components within IMD 16. In some examples, inductance 124 may include a parasitic inductance attributed to any combination of the following components: (1) ribbon bonds 80; (2) conductive traces 88; and/or (3) conductive traces 90. The actual or parasitic inductance of other components may be included within inductance 124. For example, other components upstream of channel capacitors 84 may contribute to inductance 124 including the parasitic inductance of feedthrough conductors and/or interconnect ribbons 74.

In any case, an inductance value of L may represent the combined parasitic or actual inductance of any components included within inductance 124. Inductance 124 has a first terminal that is electrically coupled to input terminal node 132A, and a second terminal that is electrically coupled to node 134.

Resistance 126 may correspond to the parasitic and/or actual resistance of one or more electrical components within IMD 16. Similar to inductance 124, resistance 126 may, in some examples, include a parasitic resistance attributed to any combination of the following components: (1) ribbon bonds 80; (2) conductive traces 88; and/or (3) conductive traces 90. In additional examples, the parasitic or actual resistance of other components may be included within resistance 126. The parasitic resistance value of $R_1$ may represent the combined actual or parasitic resistance of any components included within resistance 126. Resistance 126 has a first terminal that is electrically coupled to node 134, and a second terminal that is electrically coupled to output terminal node 136A.

In additional examples, electrical network 120 may have an additional discrete resistor and/or resistive component that is placed in series with resistance 126. In other words, one of the terminals of the discrete resistor and/or resistance may be electrically coupled to one of the terminals of resistor 126. In such cases, the resistance value $R_1$ may correspond to an effective resistance that is the combination of the parasitic resistance and the actual resistance of the additional resistance component.

Channel capacitance 128 may correspond to the capacitance of one or more of the channel capacitors 84 located on circuit board 76. Channel capacitance 128 has a capacitance value of $C_2$. Channel capacitance 128 has a first terminal that is electrically coupled to output terminal 136A, and a second terminal that is electrically coupled to output terminal 136B.

In some examples, electrical network 120 may have a parasitic capacitance between nodes 136A and 136B that is in parallel to channel capacitance 128. In such cases, the capacitance value $C_2$ of channel capacitance 128 may be an effective capacitance based on the actual channel capacitance 128 and the parallel parasitic capacitance.

Resistance 130 may correspond to the load resistance of one or more components within active circuitry 86. In some examples, resistance 130 may include the actual and/or parasitic resistance of one or more diodes in diode protection array 88. In additional examples, the parasitic or actual resistance of other components within active circuitry 86 may be included within resistance 130. The resistance value of $R_2$ may represent the combined parasitic resistance or actual resistance of any components included within active circuitry 86.

In some examples, electrical network 120 may have an additional discrete resistor and/or resistive component that has a first terminal electrically coupled to node 136A and a second terminal electrically coupled to node 136B. In other words, the additional discrete resistor and/or resistance may be in parallel with resistance 130. The additional resistance may be configured to shape the filtering characteristics of electrical network 120.

In some examples, the combined inductance and capacitance of electrical network 120 controls the resonant frequency of electrical network 120. In additional examples, the combined resistance of electrical network 120 controls the Q-factor and/or frequency bandwidth of electrical network 120.

In one non-limiting example, the capacitance value of feedthrough capacitance 122 may be approximately 1.5 nanofarads (nF), the inductance value of inductance 124 may be approximately 6 nanohenries (nH), the resistance value of the resistance 126 may be 0.8 ohms ($\Omega$), the capacitance value of the channel capacitance 128 may be 3.3 nF, and the resistance value of resistance 130 may be 1 kiloohm (k$\Omega$). These parameter values are provided for exemplary purposes, and various other combinations of parameter values are within the scope of this disclosure.

In additional examples, a source impedance may be coupled between an input node 136A of electrical network 120 and a respective electrode 40, 42, 44, 46, 48, 50, 58, 62, 64, 66. The source impedance may model the resistance or characteristic impedance of the lead conductor. One or more of the electrical components within electrical network 120 may be selected based on the characteristic impedance. For example, one or more electrical components may be selected such that the difference between the source impedance and the input resistance/impedance of electrical network 120 is below a selected threshold.

As used herein, a parasitic inductance refers to the internal inductance of a component whose primary function is something other than behaving as an inductor. In other words, the parasitic inductance is incidental to the primary function of the component. For example, the primary function of the ribbon bonds 80 and the conductive traces 88, 90, may in some cases, be to provide a conductive pathway between two components within IMD 16. In such examples, any inductance produced across the terminals of these components is incidental to the primary purpose/function of these components as conductors. Thus, any such inductance may be referred to as a parasitic inductance. Similarly, a parasitic resistance refers to the internal resistance of a component whose primary function is something other than behaving as a resistor. Likewise, a parasitic capacitance refers to the internal capacitance of a component whose primary function is something other than behaving as a capacitor.

In contrast, an actual inductance may refer to the inductance of a component whose primary function is to behave as an inductor. For example, a lumped inductor may, in some examples, have the primary function of behaving like an inductor. In such examples, the inductance would be referred to as an actual inductance. Similarly, an actual resistance may refer to the resistance of a component whose primary function is to behave as a resistor. Likewise, an actual capacitance may refer to the capacitance of a component whose primary function is to behave as a capacitor. Any determination of whether an inductance, resistance, or capacitance is parasitic or actual may be based upon the context and function of the components within a given circuit.

A reactive component may refer to a component that has an actual reactance (i.e., a component whose primary function is to produce a reactance between its terminals). For example, a capacitor may have the primary function of producing a capacitance between its terminals, and an inductor may the primary function of producing an inductance between its terminals. The reactance type for a reactive component may refer to whether a component is an inductor or a capacitor. The reactance type of a reactance may refer to whether the reactance is inductive or capacitive. Accordingly, a parasitic reactance, as used herein, may refer to a reactance produced by a reactive component where the reactance type of the reactance is different from the reactance type of the component itself. For example, a parasitic inductance may refer to an inductance produced by a capacitor. Similarly, a parasitic capacitance may refer to a capacitance produced by an inductor.

According to this disclosure, several different techniques are provided for selecting parameter values corresponding to feedthrough capacitor 122, inductance 124, resistance 126, channel capacitance 128 and/or resistance 130. These parameter values may be configured to control lead heating effects, RF rectification, device heating and/or other effects caused by a disruptive energy field proximate to IMD 16.

In some examples, the parasitic inductance 124 may be determined for one or more components, such as, e.g., ribbon bond 80 and/or conductive trace 88. Then, a channel capacitance 128 may be selected based on the parasitic inductance 124. The selected channel capacitance 128 and the parasitic inductance 124 may work together to cause electrical network 120 to resonate at a resonant frequency.

In additional examples, a reactance may be determined for one or more components, such as, e.g., feedthrough capacitance 122 and/or channel capacitance 128. Then, a parasitic inductance of one or more components may be configured based on the reactance. In some examples, the parasitic inductance may be configured by selecting a length of ribbon bond 80 and/or conductive traces 88. In additional examples, the parasitic inductance may be configured by selecting a width or diameter of ribbon bond 80 and/or conductive trances 88. In further examples, a combination of length and width/diameter may be used to adjust the parasitic inductance. The channel capacitance 128 and the configured inductance 124 may work together to cause electrical network 120 to resonate at a resonant frequency. In further examples, the reactance for one or more components and the parasitic inductance for one or more components may be simultaneously configured such that the components work together to cause electrical network 120 to resonate at a given frequency.

In general, the resonant frequency may refer to a frequency where the effective input impedance of electrical network 120 matches the effective impedance of a lead 18, 20, 22 that is electrically coupled to input terminals 132A, 132B. The components within electrical network 120 may be configured such that the resonant frequency is proximate to a frequency of the electromagnetic energy source and/or imaging modality. In some examples, the resonant frequency may be substantially equal to the frequency of the electromagnetic energy source and/or imaging modality. In other examples, the resonant frequency may be offset from the frequency of the electromagnetic energy source and/or imaging modality.

In some examples, one or both of the channel capacitance 128 and inductance 124 parameter values may be configured based on the following equation:

$$f_R = \frac{1}{2\pi\sqrt{L \cdot C_2}} \quad (1)$$

where L is the inductance 124, $C_2$ is the channel capacitance 128, and $f_R$ is the resonant frequency. In general, the techniques of this disclosure allow for any parameter to be selected if the other two parameters are known or are defined as constraints. For example, if a desired resonant frequency and an inductance 124 are specified, then the channel capacitance 128 may be determined based on equation (1). The techniques in this disclosure also allow for any two parameters to be selected if the remaining parameter is known or defined as a constraint. For example, if a desired resonant frequency is specified, then inductance 124 and channel capacitance 128 may be determined based on equation (1).

In additional examples, one or more of the feedthrough capacitance 122, channel capacitance 128 and inductance 124 parameter values may be configured based on the following equations:

$$f_R = \frac{1}{2\pi\sqrt{L \cdot C}}, C = \frac{C_1 \cdot C_2}{C_1 + C_2} \quad (2)$$

where L is the inductance 124, $C_1$ is the feedthrough capacitance, $C_2$ is the channel capacitance 128, C is the effective capacitance of the feedthrough capacitance and channel capacitance, and $f_R$ is the resonant frequency. Similar to equation (1), the techniques of this disclosure allow for any combination of parameters to be selected if the remaining parameters are known or are defined as constraints. For example, if the feedthrough capacitance 122, the resonant frequency, and the inductance 124 are specified, the channel capacitance 128 may be determined based on equation (2).

In additional examples, a lumped or discrete inductor may be placed in electrical network 120 in series with parasitic inductor 124 to produce a combined inductance, which may be substituted into the parasitic inductance (L) of equations (1) and (2). By adding a lumped inductor to electrical network 120, the range of capacitance values may be brought into a range more suitable for implementation.

In some examples, the resistance values for resistance 126 may be selected to control a magnitude of the resonance. In additional examples, an inductance 124 may be selected in conjunction with resistance 126 to control a Q-factor of the resonance. The Q-factor of a resonance may refer to how steeply or quickly the resonance rises and/or falls across a range of frequencies (e.g., the slope of the resonance). For example, the Q-factor of the resonance may refer to center frequency of the resonance divided by the bandwidth of the resonance. The bandwidth of the resonance may be determined by finding the cutoff frequency on each side of the resonance. In some examples, the cutoff frequencies may be the frequencies at which the energy or power is 3 dB above and/or below the resonance peak.

In further examples, one or more components within electrical network 120 may be configured such that one or more of the following constraints are satisfied: (1) an amount of energy reflected by electrical network 120 along leads 18, 20, 22 is below a first threshold; (2) an amount of energy transferred by electrical network 120 to active circuitry 86 is below a second threshold; and/or (3) an amount of energy dissipated by electrical network 120 is below a third threshold. The first threshold may be used to control lead heating effects produced when IMD 16 is in the presence of or subject to energy emitted by an electromagnetic energy source. The second threshold may be used to control RF rectification that may occur when IMD 16 is in the presence of or subject to energy emitted by an electromagnetic energy source. The third threshold may be used to control device heating that may occur when IMD 16 is in the presence of or subject to energy emitted by an electromagnetic energy source.

In some examples, if any two constraints are selected, parameter values may be configured to satisfy the remaining constraint. For example, if thresholds are selected to control lead heating effects and RF rectification, then an amount of energy dissipated by electrical network 120 may be configured such that the two thresholds are satisfied. For example, parasitic and/or actual resistances within electrical network 120 may be adjusted to increase the amount of energy dissipated by electrical network 120. In additional examples, if all three constraints are specified, the techniques of this disclosure may be used to find component parameters that satisfy all three constraints.

Figure 6A:
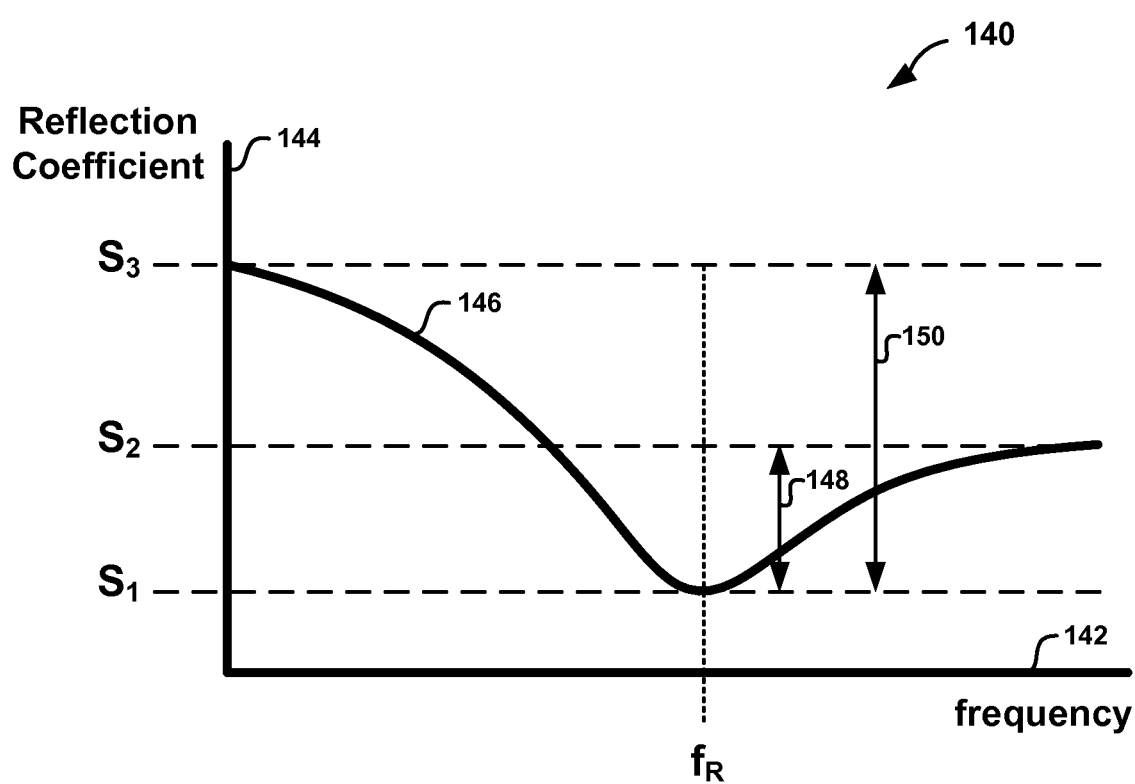
FIGS. 6A and 6B are charts illustrating example reflection coefficient plots for an electrical network model according to this disclosure.
Figure 6B:
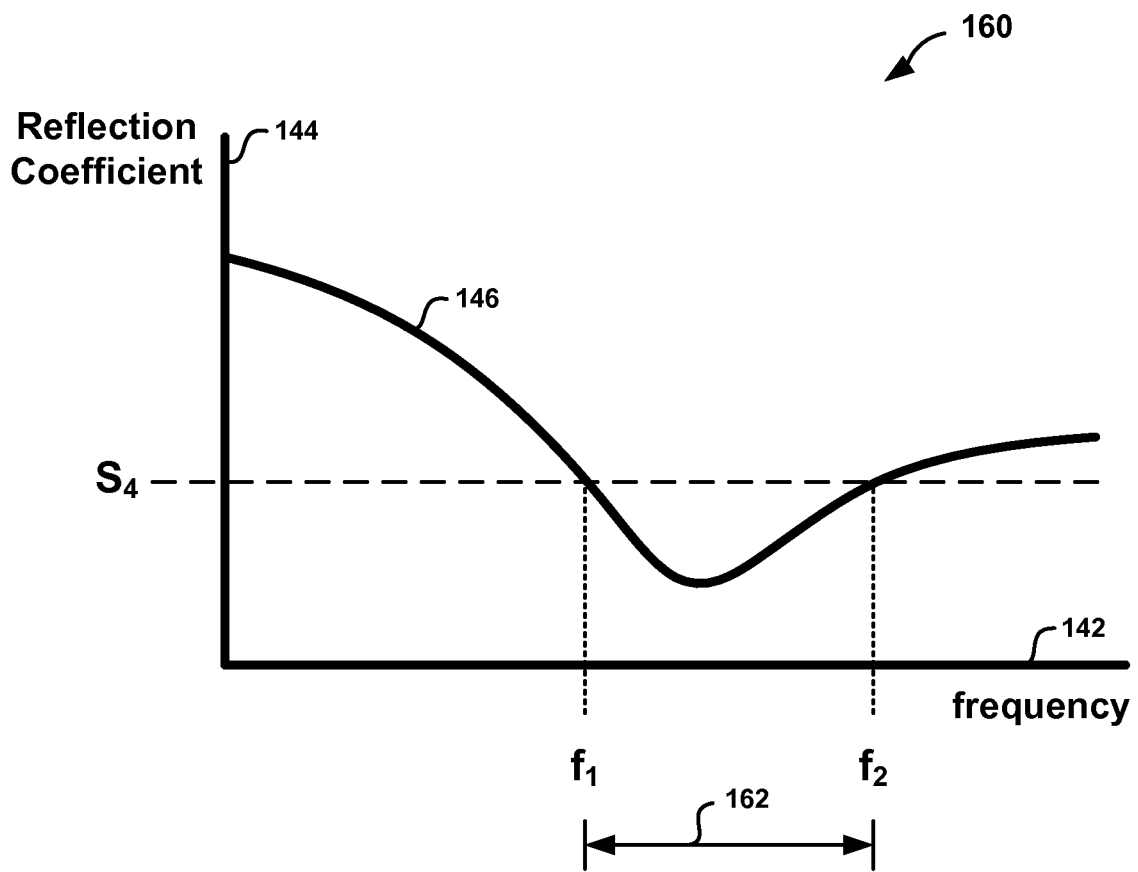

FIGS. 6A & 6B are charts 140, 160 illustrating an example reflection coefficient plot for electrical network model 120 according to this disclosure. Both of the charts 140, 160 include a frequency axis 142 that increases from left to right, a reflection coefficient axis 144 that increases from bottom to top, and a reflection coefficient plot 146 for a range of frequencies. The reflection coefficient axis 146 is plotted in units of decibels (dB).

In general, the reflection coefficient for electrical network 120 may be calculated according to the following equation:

$$S = \frac{Z_{inp} - Z_0}{Z_{inp} + Z_0} \quad (3)$$

where $Z_{inp}$ represents the effective input impedance of electrical network 120 (i.e., the effective impedance of electrical network 120 when looking "into" input nodes 132A, 132B), $Z_0$ represents the characteristic impedance of the electrical lead, and S represents the reflection coefficient. In some examples, the reflection coefficient may correspond to the $S_{11}$ two-port network parameter.

The reflection coefficient plot shown in FIG. 6A has a resonance at frequency $f_R$. At the resonant frequency, the difference between $Z_{inp}$ and $Z_0$ may be substantially reduced. In some examples, $Z_{inp}$ and $Z_0$ may be substantially equal. The reduction in the difference between $Z_{inp}$ and $Z_0$ may cause the amount of energy reflected along the lead by electrical network 120 to rapidly approach zero. In other words, at the resonant frequency, a substantial amount of the energy is either transferred to active circuitry 86 or dissipated by electrical network 120. Distances 148 and 150 illustrate two distances that may be defined as magnitudes of the resonance. Distance 148 is defined as the difference between the peak resonance reflection coefficient ($S_1$) and the steady-state reflection coefficient for frequencies higher than the resonance ($S_2$). Distance 150 is defined as the difference between the peak resonance reflection coefficient ($S_1$) and the steady-state reflection coefficient for frequencies lower than the resonance ($S_3$). In some examples, the magnitude of the resonance may be defined as the average of distances 148, 150. In other examples, the magnitude of the resonance may be based on the value of the peak resonance reflection coefficient and some other reflection coefficient at a non-resonant frequency (e.g., a cutoff frequency). According to the techniques in this disclosure, resistance 126 may be configured and/or adjusted to achieve a desired magnitude for the resonance.

The reflection coefficient plot shown in FIG. 6B has two cutoff frequencies $f_1$ and $f_2$. The cutoff frequencies may be the frequencies at which the reflection coefficient is a certain level above or below the peak resonance reflection coefficient ($S_1$). As shown in FIG. 6B, the cutoff frequencies are determined based on cutoff reflection coefficient value ($S_4$). In some examples, the cutoff reflection coefficient value may be 3 dB above and/or below the peak reflection coefficient at the resonant frequency. A bandwidth of the resonance may be determined by finding the difference between the cutoff frequencies ($f_2 - f_1$). The quality factor (Q-factor) of a resonance may refer to center frequency of the resonance ($f_R$) divided by the bandwidth of the resonance. The Q-factor may refer to how steeply or quickly the resonance rises and/or falls across a range of frequencies (e.g., a slope of the resonance curve). According to the techniques in this disclosure, inductance 124 may be configured and/or adjusted to achieve a desired Q-factor for the resonance.

Figure 7:
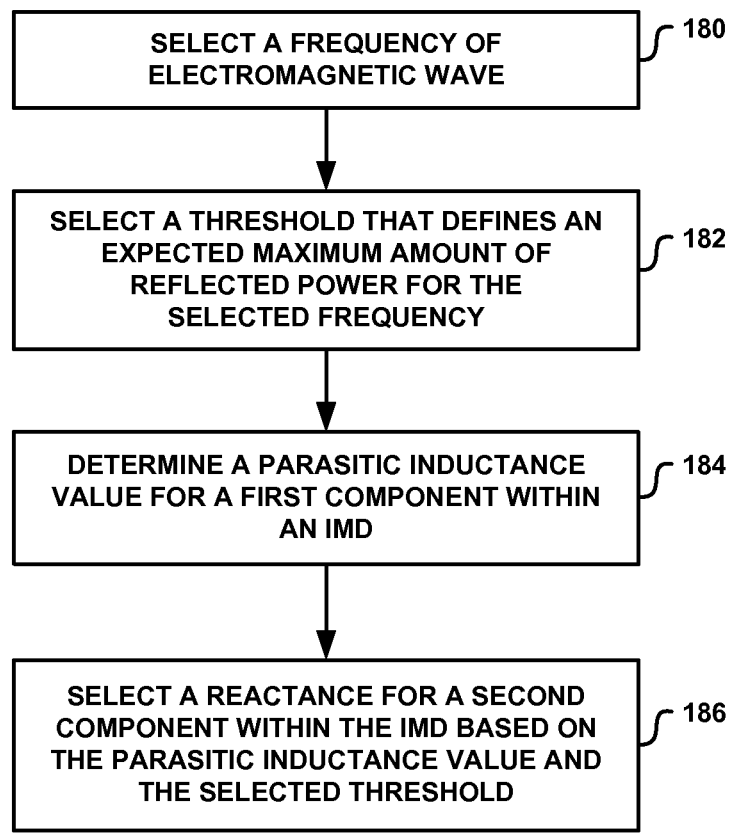
FIG. 7 is a flow diagram illustrating an example technique for controlling lead heating effects according to this disclosure.

FIG. 7 is a flow diagram illustrating an example technique for reducing lead heating effects according to this disclosure. According to FIG. 7, a frequency of electromagnetic wave is selected (180). The selected frequency may correspond to the frequency of an electromagnetic energy source that produces or emits EMI. The electromagnetic energy source may, in some examples, be a medical imaging modality, such as, e.g., an MRI imaging modality. In some examples, the selected frequency may be a range of frequencies. In additional examples, rather than selecting a frequency of electromagnetic wave, a frequency of induced current may be selected.

A threshold that defines a maximum amount of reflected energy for the selected frequency may also be selected (182). The threshold may correspond to a level of reflected energy below which lead heating effects are acceptable when IMD 16 is placed in the presence of (e.g., subject to) a disruptive energy field of a particular frequency. In additional examples, the threshold may define a maximum amount of current induced within a lead of IMD 16 when IMD 16 is placed in the presence of a disruptive energy field.

A parasitic inductance value for a first component within IMD 16 is determined (184). In some examples, the first component may include one or more ribbon bonds 80 within IMD 16. In some cases, the one or more ribbon bonds 80 may be laser ribbon bonds. In other examples, the first component may include one or more conductive traces 88, 90 within IMD 16. In general, the first component may include any combination of components within IMD 16 that has a parasitic inductance.

A reactance for a second component within IMD 16 may be selected based on the parasitic inductance value and the selected threshold (186). For example, the reactance of the second component may be selected based on the parasitic inductance value such that an amount of energy reflected along the lead in response to an electromagnetic energy source is below the selected threshold. As another example, the reactance for the second component may be selected such that a resonance occurs at a frequency proximate the selected frequency. By causing a resonance at a frequency proximate to the selected frequency, the amount of energy reflected along the lead in response to an electromagnetic energy source may be reduced. In additional examples, the reactance of the second component may be selected based on the parasitic inductance value such that an amount of current induced within the lead is lead below the selected threshold.

In some examples, the second component may be a capacitor, e.g. channel capacitor 84, and the reactance may be a capacitance of the capacitor. In such examples, equation (1) may be used to select the appropriate value of channel capacitance based on the parasitic inductance and a desired resonant frequency. Equation (2) may be also used to select the appropriate value of channel capacitance based on the parasitic inductance, the capacitance of feedthrough capacitor 72, and a desired resonant frequency.

Figure 8:
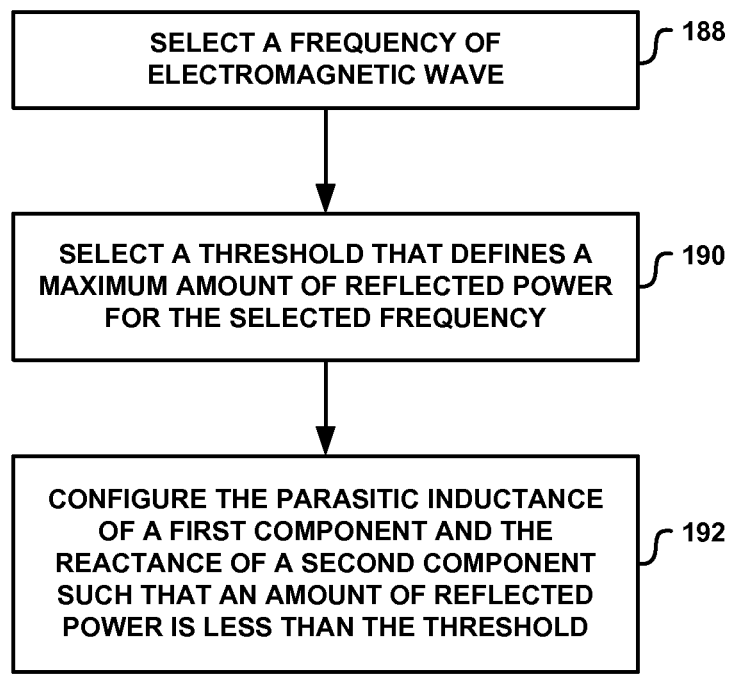
FIG. 8 is a flow diagram illustrating another example technique for controlling lead heating effects according to this disclosure.

FIG. 8 is a flow diagram illustrating another example technique for reducing lead heating effects according to this disclosure. Similar to the technique shown in FIG. 7, a frequency of electromagnetic wave or induced current is selected (188). A threshold that defines a maximum amount of reflected energy for the selected frequency may also be selected (190). Then, a parasitic inductance of a first component and a reactance of a second component may be configured such that an amount of reflected energy is less than the threshold (192). In some examples, the first component may include one or more ribbon bonds 80 and/or one or more conductive traces 88, 90 within IMD 16. In such cases, the parasitic inductance of the first component may be configured by adjusting a length and/or width of the first component. For example, a length and/or width of ribbon bond 80 and/or conductive traces 88, 90 may be configured to produce a desired parasitic inductance.

In some examples, an inductor may be placed in series with the first component. The combination of the actual inductance of the inductor and the parasitic inductance of the first component may produce an effective inductance that can allow for a better selection of reactance values (e.g., capacitance values).

Figure 9:
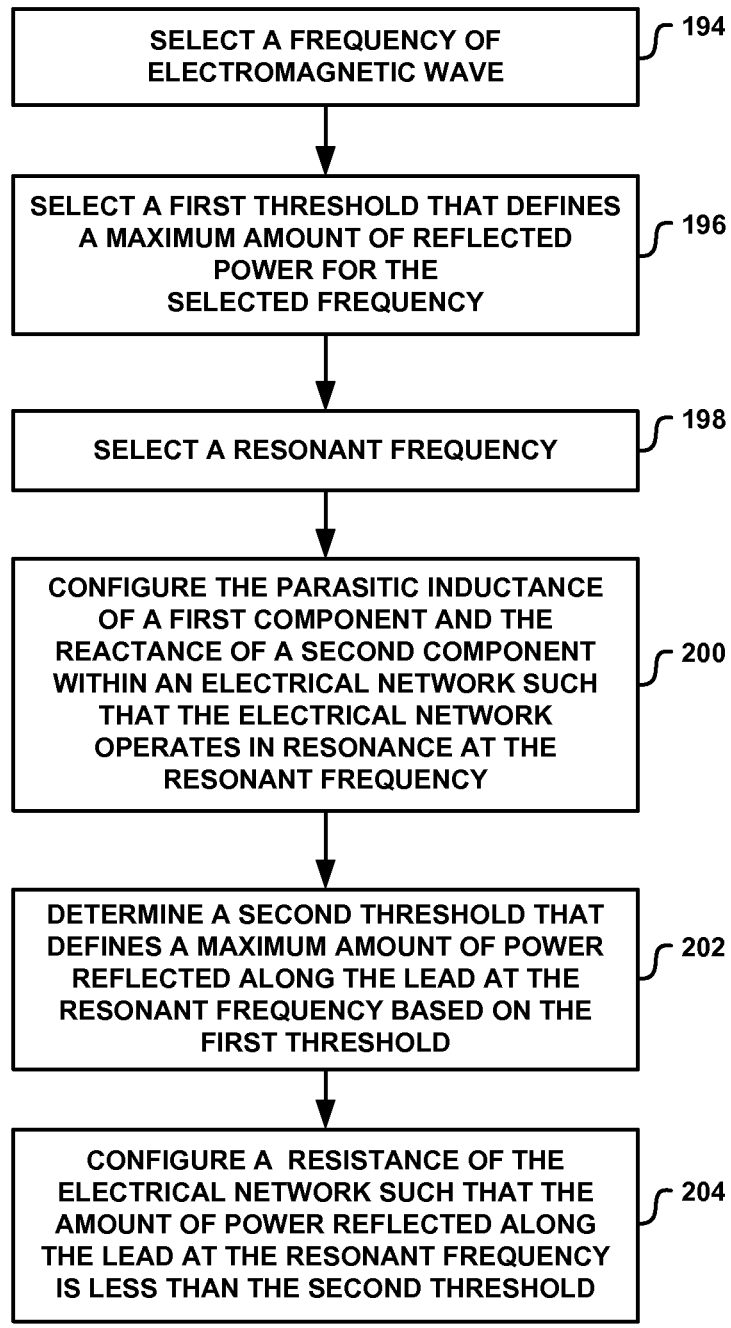
FIG. 9 is a flow diagram illustrating another example technique for controlling lead heating effects according to this disclosure.

FIG. 9 is a flow diagram illustrating another example technique for reducing lead heating effects according to this disclosure. Similar to the technique shown in FIG. 7, a frequency of electromagnetic wave or induced current is selected (194). A first threshold that defines a maximum amount of reflected energy for the selected frequency may also be selected (196). A resonant frequency for an electrical network that includes a first component and a second component may be selected (198). In some examples, the resonant frequency may be selected such that the resonant frequency occurs at a frequency proximate to or substantially equal to the selected frequency of electromagnetic wave. Then, the parasitic inductance of a first component and the reactance of a second component may be configured such that the electrical network operates in resonance at the resonant frequency (200).

A second threshold may be determined based on the first threshold (202). The second threshold may define a maximum amount of reflected energy at the resonant frequency. For example, the second threshold may define a resonance magnitude that is needed to achieve the reflected energy level specified by the first threshold. Then, a resistance within the electrical network may be configured such that the amount of energy reflected along the lead at the resonant frequency is less than the second threshold. (204).

In some examples, the resistance configured in step 204 may be a parasitic resistance of the first component. In another example, the resistance configured in step 204 may be an effective input resistance (i.e., real input impedance) for electrical network 120.

In additional examples, the parasitic inductance of the first component may be adjusted in addition to or in lieu of the resistance to cause the amount of energy reflected along the lead at the resonant frequency to be less than the second threshold. The parasitic inductance of the first component may be configured to cause the electrical network 120 to have a particular bandwidth or Q-factor, which will in turn allow the desired amount of reflected energy to be achieved. For example, when the first component is a conductor, the length and/or width may be configured to produce a particular parasitic inductance.

Figure 10:
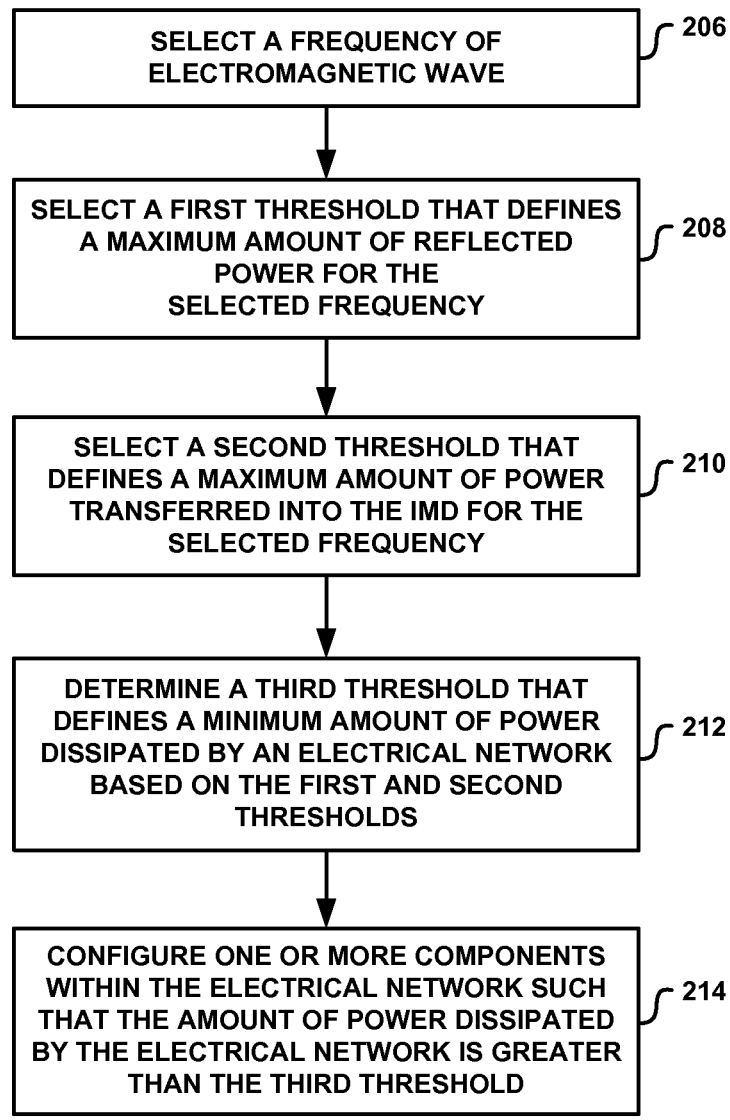
FIG. 10 is a flow diagram illustrating an example technique for controlling lead heating effects and power rectification according to this disclosure.

FIG. 10 is a flow diagram illustrating an example technique for controlling lead heating effects and power rectification according to this disclosure. A frequency of electromagnetic wave is selected (206). A first threshold that defines a maximum amount of reflected energy for the selected frequency may also be selected (208). A second threshold that defines a maximum amount of energy transferred into IMD 16 may be selected for the selected frequency (210). A third threshold that defines a minimum amount of energy dissipated by an electrical network may be determined based on the first and second thresholds (212). One or more components within the electrical network may be configured such that an amount of energy dissipated by the electrical network is greater than the third threshold (214). The one or more components may include the first and second components described above with respect to FIG. 7.

Figure 11:
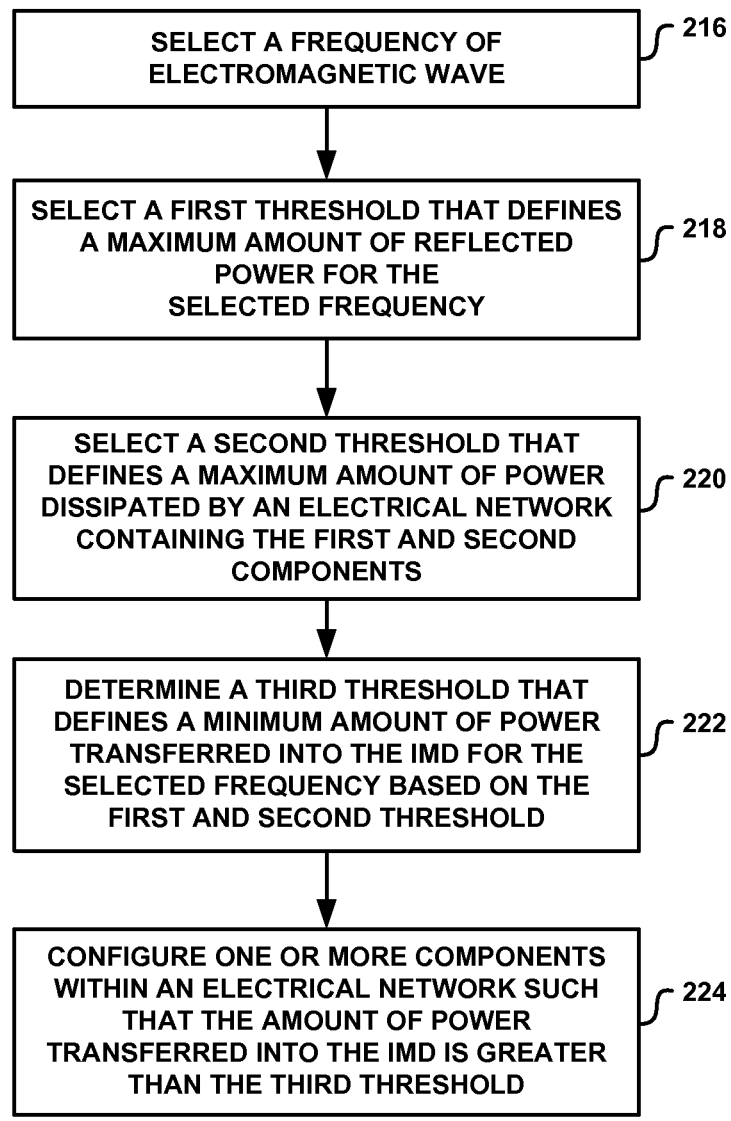
FIG. 11 is a flow diagram illustrating an example technique for controlling lead heating effects and device heating effects according to this disclosure.

FIG. 11 is a flow diagram illustrating an example technique for controlling lead heating effects and device heating effects according to this disclosure. A frequency of electromagnetic wave is selected (216). A first threshold that defines a maximum amount of reflected energy for the selected frequency may also be selected (218). A second threshold that defines a maximum amount of energy dissipated by an electrical network may be selected (220). A third threshold that defines a minimum amount of energy transferred into IMD 16 may be determined based on the first and second thresholds (222). One or more components within the electrical network may be configured such that an amount of energy transferred into IMD 16 is greater than the third threshold (224). The one or more components may include the first and second components described above with respect to FIG. 7.

Figure 12:
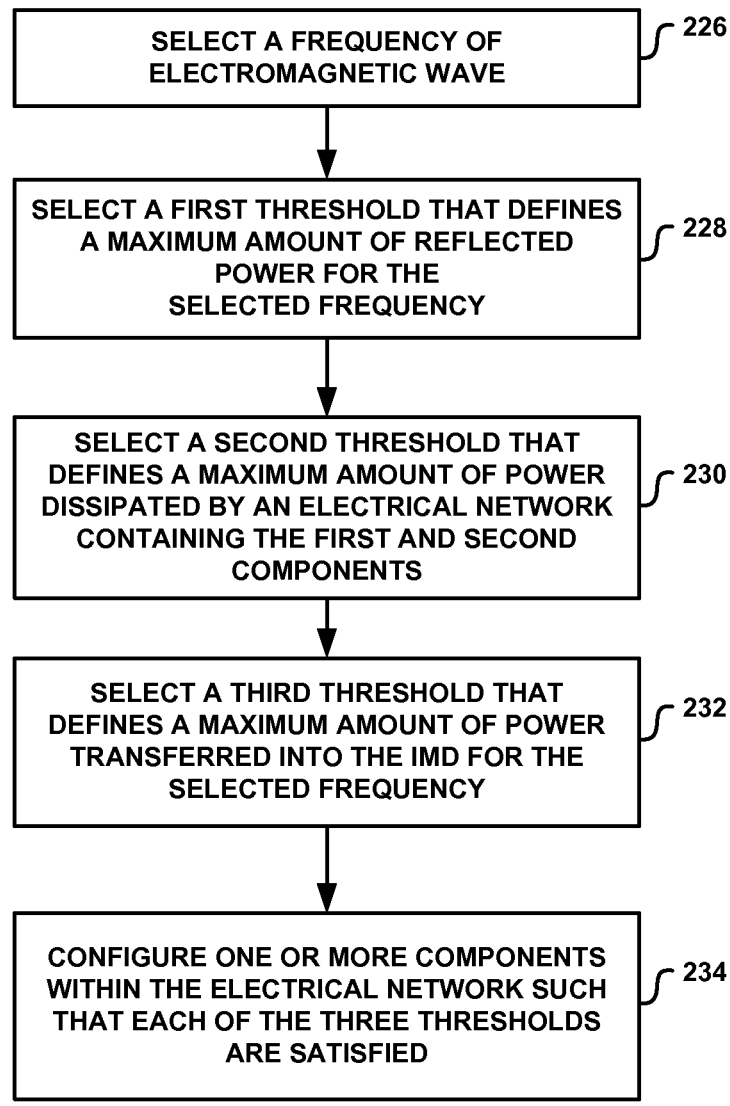
FIG. 12 is a flow diagram illustrating an example technique for controlling lead heating effects, power rectification, and device heating effects according to this disclosure.

FIG. 12 is a flow diagram illustrating an example technique for controlling lead heating effects, power rectification, and device heating effects according to this disclosure. A frequency of electromagnetic wave is selected (226). A first threshold that defines a maximum amount of reflected energy for the selected frequency may also be selected (228). A second threshold that defines a maximum amount of energy dissipated by an electrical network may be selected (230). A third threshold that defines a maximum amount of energy transferred into IMD 16 may also be selected (232). One or more components within the electrical network may be configured such that all three thresholds are satisfied (234).

With regard to the flow diagrams in FIGS. 7-12, it should be noted that the ordering of steps in the flow diagram are merely exemplary, and that other orderings are within the scope of this disclosure. In addition, it should be recognized that steps may be removed and/or deleted from the diagrams without departing from this disclosure.

In some examples, the thresholds described with respect to FIGS. 7-12 of this disclosure may refer to a voltage or current amplitudes as opposed to an amount of energy, and the components may be configured such that the voltage or current amplitudes are below the selected threshold. In general, any metric associated with the reflected wave, lead heating effects, RF rectification, and device heating effects may be used as the design criteria for the parasitic inductance and reactance without departing from the scope of this disclosure.

The techniques of this disclosure may be implemented by an IMD that is configured to provide pacing therapy, and/or cardio-version shocks. In addition, the techniques in this disclosure may also be applied to other types of IMDs. For example, the techniques in this disclosure may be applied to neurostimulators, including deep brain stimulators, spinal cord stimulators, peripheral nerve stimulators, pelvic floor stimulators, gastro-intestinal stimulators, or the like.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), static RAM (SRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   determining a parasitic inductance for a first component within an implantable medical device (IMD) that includes a lead that includes one or more electrodes; and
   selecting a reactance for a second component within the IMD based on the parasitic inductance such that an amount of energy reflected along the lead in response to energy produced by an electromagnetic energy source is below a selected threshold.

2. The method of claim 1, wherein the first component comprises at least one of a ribbon bond and a conductive trace.

3. The method of claim 1, wherein the first component is coupled between a feedthrough assembly of the IMD and a circuit board contained within the IMD.

4. The method of claim 1, wherein the first component is coupled between a pad disposed on a circuit board contained within the IMD and a channel capacitor disposed on the circuit board.

5. The method of claim 1, wherein an inductor is coupled in series with the first component, and wherein selecting the reactance for the second component comprises selecting the reactance for the second component based on the parasitic inductance and an inductance value of the inductor.

6. The method of claim 1, wherein the IMD comprises a circuit board having a pad, a diode, and a conductive trace disposed thereon, wherein the conductive trace is coupled between the pad and the diode, and wherein the second component is a capacitor coupled between the conductive trace and a ground voltage for the circuit board.

7. The method of claim 6, wherein the first component comprises the conductive trace.

8. The method of claim 6, wherein the IMD further comprises a feedthrough assembly and a ribbon bond coupled between the feedthrough assembly and the pad, and wherein the first component comprises the ribbon bond.

9. The method of claim 6, wherein the IMD further comprises a housing and a conductive feedthrough pin, wherein a feedthrough capacitor is coupled between the feedthrough pin and the housing of the IMD.

10. The method of claim 9, wherein selecting the reactance for the second component comprises selecting the capacitance of the capacitor and the capacitance of the feedthrough capacitor based on the parasitic inductance.

11. The method of claim 10, wherein the selected threshold defines a maximum amount of energy reflected by the IMD when the IMD is subject to the energy produced by the electromagnetic energy source.

12. The method of claim 11, wherein the threshold is a first threshold, wherein the method further comprises selecting a second threshold that defines a maximum amount of energy transferred to a diode within the IMD, and wherein selecting the reactance for the second component comprises selecting the reactance for the second component such that an amount of energy reflected along the lead in response to the energy produced by the electromagnetic energy source is below the first threshold and an amount of energy transferred to the diode is below the second threshold.

13. The method of claim 11, wherein the threshold is a first threshold, wherein the method further comprises selecting a second threshold that defines a maximum amount of energy dissipated by the first component and the second component, and wherein selecting the reactance for the second component comprises selecting the reactance for the second component such that an amount of energy reflected along the lead in response to the energy produced by the electromagnetic energy source is below the first threshold and an amount of energy dissipated by an electrical network that includes the first component and the second component is below the second threshold.

14. The method of claim 1, wherein selecting the reactance for the second component comprises selecting the reactance such that the first component and the second component produce a resonance at a resonant frequency proximate to a frequency of the energy produced by the electromagnetic energy source.

15. The method of claim 14, wherein the selected threshold is a first threshold, and wherein the method further comprises:
   selecting the first threshold to define a maximum amount of energy reflected by the IMD at the frequency of the energy produced by the electromagnetic energy source;

determining a second threshold that defines a maximum amount of energy reflected along the lead at the resonant frequency based on the first threshold; and configuring a parasitic resistance of the first component such that the amount of energy reflected along the lead at the resonant frequency is less than the second threshold.

16. The method of claim 15, wherein configuring the parasitic resistance of the first component comprises configuring the parasitic resistance and the parasitic inductance of the first component such that the amount of energy reflected along the lead at the resonant frequency is less than the second threshold.

17. The method of claim 1, wherein the electromagnetic energy source comprises an imaging modality.

18. The method of claim 17, wherein the imaging modality comprises a magnetic resonance imaging modality.

19. The method of claim 1, wherein the IMD comprises an implantable cardiac device.

20. An implantable medical device (IMD) comprising:
an implantable lead that includes one or more electrodes;
a first component having a parasitic inductance; and
a second component having a reactance selected based on the parasitic inductance such that an amount of energy reflected along the lead in response to energy produced by an electromagnetic energy source is below a selected threshold.

21. The device of claim 20, wherein the first component comprises at least one of a ribbon bond and a conductive trace.

22. The device of claim 20, further comprising:
a feedthrough assembly; and
a circuit board coupled to the feedthrough assembly via the first component.

23. The device of claim 20, further comprising:
a circuit board having a pad and a channel capacitor disposed thereon, wherein the channel capacitor is coupled to the pad via the first component.

24. The device of claim 20, further comprising:
an inductor coupled in series with the first component, wherein the reactance for the second component is selected based on the parasitic inductance and an inductance value of the inductor.

25. The device of claim 20, further comprising:
a circuit board comprising:
a pad disposed on the circuit board; and
a diode disposed on the circuit and coupled to the pad via a conductive trace, wherein the second component comprises a capacitor coupled between the conductive trace and a ground voltage for the circuit board.

26. The device of claim 25, wherein the first component comprises the conductive trace.

27. The device of claim 25, further comprising:
a feedthrough assembly; and
a ribbon bond coupled between the feedthrough assembly and the pad, wherein the first component comprises the ribbon bond.

28. The device of claim 25, further comprising:
a housing;
a conductive feedthrough pin; and
a feedthrough capacitor coupled between the feedthrough pin and the housing of the IMD.

29. The device of claim 28, wherein the capacitance of the capacitor and the capacitance of the feedthrough capacitor are selected based on the parasitic inductance.

30. The device of claim 29, wherein the selected threshold defines a maximum amount of energy reflected by the IMD when the IMD is subject to the energy produced by the electromagnetic energy source.

31. The device of claim 30, wherein the selected threshold is a first threshold, wherein the reactance for the second component is selected such that an amount of energy reflected along the lead in response to the energy produced by the electromagnetic energy source is below the first threshold and an amount of energy transferred to the diode is below a second threshold, and wherein the second threshold is based on a maximum amount of energy transferred to the diode.

32. The device of claim 30, wherein the selected threshold is a first threshold, wherein the reactance for the second component is selected such that an amount of energy reflected along the lead in response to the energy produced by the electromagnetic energy source is below the first threshold and an amount of energy dissipated by the first component and the second component is below a second threshold, and wherein the second threshold is based on a maximum amount of energy dissipated by an electrical network that includes the first component and the second component.

33. The device of claim 20, wherein the reactance for the second component is selected such that the first component and the second component produce a resonance at a resonant frequency proximate to a frequency of the energy produced by the electromagnetic energy source.

34. The device of claim 33, wherein the selected threshold is a first threshold, wherein the first threshold defines a maximum amount of energy reflected by the IMD at the frequency of the energy produced by the electromagnetic energy source, wherein a parasitic resistance of the first component is configured such that an amount of energy reflected along the lead at the resonant frequency is less than a second threshold, and wherein the second threshold defines a maximum amount of energy reflected along the lead at the resonant frequency based on the first threshold.

35. The device of claim 34, wherein the parasitic resistance and parasitic inductance of the first component are configured such that the amount of energy reflected along the lead at the resonant frequency is less than the second threshold.

36. The device of claim 20, wherein the electromagnetic energy source comprises an imaging modality.

37. The device of claim 36, wherein the imaging modality comprises a magnetic resonance imaging modality.

38. The device of claim 20, wherein the IMD comprises an implantable cardiac device.

* * * * *